(12) United States Patent
Natsuka et al.

(10) Patent No.: US 7,723,080 B2
(45) Date of Patent: May 25, 2010

(54) MURINE α (1,3) FUCOSYLTRANSFERASE FUC-TVII, DNA ENCODING THE SAME, METHOD FOR PREPARING THE SAME, ANTIBODIES RECOGNIZING THE SAME, IMMUNOASSAYS FOR DETECTING THE SAME, PLASMIDS CONTAINING SUCH DNA, AND CELLS CONTAINING SUCH A PLASMID

(76) Inventors: Shunji Natsuka, 1423 Natalie La., #79, Ann Arbor, MI (US) 48105; Kevin Gersten, 1826 N. 57th St., Seattle, WA (US) 98103-5913; John B. Lowe, 830 Watershed Dr., Ann Arbor, MI (US) 48105

( * ) Notice: Subject to any disclaimer, the term of this patent is extended or adjusted under 35 U.S.C. 154(b) by 1100 days.

(21) Appl. No.: 10/700,505

(22) Filed: Nov. 5, 2003

(65) Prior Publication Data

US 2004/0063178 A1    Apr. 1, 2004

Related U.S. Application Data

(60) Division of application No. 09/784,077, filed on Feb. 16, 2001, now Pat. No. 6,693,183, which is a continuation of application No. 08/613,098, filed on Mar. 8, 1996, now abandoned.

(51) Int. Cl.
| | |
|---|---|
| *C12P 19/18* | (2006.01) |
| *C12P 19/26* | (2006.01) |
| *C12P 1/00* | (2006.01) |
| *C12N 9/00* | (2006.01) |

(52) U.S. Cl. .............................. 435/97; 435/84; 435/41; 435/183

(58) Field of Classification Search ................... 435/97, 435/84, 41, 183
See application file for complete search history.

(56) References Cited

U.S. PATENT DOCUMENTS 5,858,752 A * 1/1999 Seed et al. ................... 435/193

OTHER PUBLICATIONS

Sasaki et al. Expression cloning of a novel alpha 1,3-fucosyltransferase that is involved in biosynthesis of the sialyl Lewis x carbohydrate determinants in leukocytes. 1994, J. Biol. Chem. 269:14730-14737.*

* cited by examiner

*Primary Examiner*—Taeyoon Kim
(74) *Attorney, Agent, or Firm*—Nada Jain, P.C.

(57) ABSTRACT

A gene which encodes a murine leukocyte α(1,3)fucosyltransferase capable of synthesizing the sialyl Lewis x determinant has been cloned.

10 Claims, 8 Drawing Sheets

```
acaaacaggaaggacagcaggctctggcagccagaagcctgtggccccaagctggcaggatggccccCttcctgcaggtc      80
ccccacagccttctgggttcctgacacgagagaagaggtggggcggggtgaagtgaactctgaagccaaaatgtgactct     160
cctggggtcaccagcttggggagaggtgaagaaagatgccggggcggaaacaaaggggcagatatcactatggttatctt     240
actaagcacagagtaactgaaaaagcaagggtaccgctgcccacctcgtgcccaccttacgttatacctcaaaccagcta     320
gatagtttctgatggcacccataccctccctcccctttaggcattgcgcaagctctccaccacaatctggaagttatac      400
cctgcgaggggatgggcagggcacttctgaggtgccaatcagcctgcactcgcctctgccctggCCATGGCACTGCTgtc      480
agtttcttggtacctgtcctcaacagcagccttgtcacgtgagactatggctggcggtgggggtggggcaggaatcctag     560
aagcacaggagtgacatagggtcgggtcgggcagagcgaagtgtaggaggtgatcccaaagggatgctggggacgatct      640
ggccaacactgtcctcccattcaaaactcCCAGTCTGGAGCTCTGGACATGGACAAGCCAGGCCTGCTATTCTCCATAC      720
AGGGCTCCATAGTGTCTGGCTCAGCAGAGTGGGGGATCTGGTGGGGATGGAGGAAGCTTAGCTAAAAGCTTTGTATAGGC     800
TGAAGCTCTGAGTGACCCTGCTGGGCCACCCTACCCTGGTCTGGGCTGGGTCATTGCATCCCCAGATTGGAAGGCTTGGT     880
GAGATGGAGAGGAACCTTGGCTACAAGCTATAGCTTTGCCCACCAGAGCCTGCTGGAGGGGAATCAAACAAGCCTGGACC     960
TGAGGCTGGGACTAGCTTTCCTGTTTCTGGAGTGGATGCCAACCCCCTGCCCACCAGCCTGCCTGTCCACGCCAGGGACA    1040
                                              M  P  T  P  C  P  P  A  C  L  S  T  P  G  T
CACAGACTCCTTCCCTTTCCAGACTGGAAAGCCCCCTCCTGGGAGAGCAGGAAGGAAGCAACCTGCAACTCTTCCAGCCC    1120
 H  R  L  L  P  F  P  D  W  K  A  P  S  W  E  S  R  K  E  A  T  C  N  S  S  P
TGGACCTTGGGCTGAACCTACAGTTCAAGgtttgtatgctcacaggtcttggcagggaaagataagaatccccagggcac    1200
 G  P  W  A  E  P  T  V  Q
cctcccccgcccccagtccactgcaggtagctcctgggtctgcccttcagggcaagtgctgacgctccatcagactg      1280
tgatggggccttttctgaggatgacaattctgagaacaaggcattttttctagaggtggcagaacagcattttgtgatgc    1360
ccgaggatctgggagcacaggtccagcttaatgagggattggaggaagtgggtatcatcattacagggagggggcctctgt    1440
ggcctcctgggaaaatgcagttgctctctttgggtggcctggggttgtgtggtggcagaggacggaggtgctcattggg    1520
ggaagggatcacttctgctcagagtgctcgcaagggcctttcctttccctgaaggcaagcaggcctcctcctcctcctct    1600
tcctccttctcctcttcctcctctttctccatatgcctagctggtcatttctagggaccagcatggttgggaaggggcc    1680
ttgtcttggccttcctcttgtctcaattccctctttgagcagaagacggggtgggtggggtaggattggatagcGGTTGA    1760
TGCCAAAGATTGAAGGGGTAGGGCGGGGCAGAAGTGGGAAGGTCCCTGGCTTCCTCACCTTGGTAGATGGTGAGGAGCCC    1840
CAGAGGTTGAGCTGAGCAGCAGCTGTGATTTCAGGGTGCCTCTGTTGGAGAGGCTGCTGTGATTTGAAAATCTTCTTTCC    1920
TTGGTGACAATTCCAGAAGGCTCCAGATGAATTGTATTGgtgagtgcctggcccttaagcagtcccagctggggatgatg    2000
           M  N  C  I
```

FIGURE 2

```
gggatttatgggtgtccctgagcctagggtgacagggcctctcctttttttttattctgcttcagGGTACCACCCCACC    2080
                                                                 G   Y   H   P   T AGGAGGCTGCGGGCCTGGGGCGGCCTAGCTGGAGGAGCAACATTCATGGTAATTTGGTTTTTCTGGCTGTGGGGATCAGC    2160
 R   R   L   R   A   W   G   G   L   A   G   G   A   T   F   M   V   I   W   F   F   W   L   W   G   S   A TCCTGGAAGTGCCCCTGTGCCTCAGTCCACACTCACCATCCTTATCTGGCACTGGCCTTTCACCAACCGGCCGCCAGAGC    2240
 P   G   S   A   P   V   P   Q   S   T   L   T   I   L   I   W   H   W   P   F   T   N   R   P   P   E TACCTGGTGACACCTGCACTCGCTATGGCATGGCCAGCTGCCGTCTGAGTGCTAACCGGAGCCTGCTAGCCAGTGCTGAT    2320
 L   P   G   D   T   C   T   R   Y   G   M   A   S   C   R   L   S   A   N   R   S   L   L   A   S   A   D GCTGTGGTCTTCCACCACCGTGAGCTGCAAACCCGGCAATCTCTCCTACCCCTGGACCAGAGGCCACACGGACAGCCTTG    2400
 A   V   V   F   H   H   R   E   L   Q   T   R   Q   S   L   L   P   L   D   Q   R   P   H   G   Q   P   W GGTCTGGGCCTCCATGGAATCGCCCAGTAATACCCATGGTCTCCATCGCTTCCGGGGCATCTTCAACTGGGTGCTGAGCT    2480
 V   W   A   S   M   E   S   P   S   N   T   H   G   L   H   R   F   R   G   I   F   N   W   V   L   S ATCGGCGTGATTCAGATATCTTTGTACCCTACGGTCGCTTGGAGCCTCTCTCTGGGCCCACATCCCCACTACCGGCCAAA    2560
 Y   R   R   D   S   D   I   F   V   P   Y   G   R   L   E   P   L   S   G   P   T   S   P   L   P   A   K AGCAGGATGGCTGCCTGGGTGATCAGCAATTTCCAGGAGCGGCAGCAGCGTGCAAAGCTGTACCGGCAGCTGGCCCCTCA    2640
 S   R   M   A   A   W   V   I   S   N   F   Q   E   R   Q   Q   R   A   K   L   Y   R   Q   L   A   P   H TCTGCAGGTGGATGTGTTCGGTCGCGCCAGCGGACGGCCCCTATGCGCTAATTGTCTGCTGCCCACTTTGGCCCGGTACC    2720
 L   Q   V   D   V   F   G   R   A   S   G   R   P   L   C   A   N   C   L   L   P   T   L   A   R   Y GCTTCTACCTGGCCTTTGAGAACTCACAGCATCGGGACTACATCACTGAGAAGTTCTGGCGCAATGCCCTGGCGGCTGGT    2800
 R   F   Y   L   A   F   E   N   S   Q   H   R   D   Y   I   T   E   K   F   W   R   N   A   L   A   A   G GCTGTACCCGTGGCGCTGGGACCTCCTCGGGCCACCTACGAGGCTTTTGTGCCACCAGATGCCTTTGTACACGTGGACGA    2880
 A   V   P   V   A   L   G   P   P   R   A   T   Y   E   A   F   V   P   P   D   A   F   V   H   V   D   D CTTCAGCTCTGCCCGTGAACTGGCTGTCTTCCTCGTCAGCATGAATGAGAGTCGTTATCGTGGCTTCTTTGCTTGGCGAG    2960
 F   S   S   A   R   E   L   A   V   F   L   V   S   M   N   E   S   R   Y   R   G   F   F   A   W   R ACCGGCTCCGTGTGCGGCTCCTGGGTGACTGGAGGGAGCGCTTCTGCACCATCTGTGCCCGCTACCCTTACTTGCCCCGC    3040
 D   R   L   R   V   R   L   L   G   D   W   R   E   R   F   C   T   I   C   A   R   Y   P   Y   L   P   R AGCCAGGTCTATGAAGACCTTGAAAGCTGGTTCCAGGCTTGAACTCCTGCTGCTGGGAGAGGCTGGATGGGTGGGAGACT    3120
 S   Q   V   Y   E   D   L   E   S   W   F   Q   A   *

GATGTTGAAACCAAAGAGCTGGGCATCCAGGCTTTTGGTCACCATGGCACTACCCCAAGGCTTTTCCTGTTCAGTGAGCA    3200

GGAATTCAGGATATAAGGAGAAGACTGGGCTGAGATACCCTGGTGGGCTTTAGAGTAGGGGCCCAGGATAAGAGACAATG    3280

AATTAATGAGGAGCATATGGGGAAGGTGGCTGAGGGTCCCTGACTTACCTTGACCCATGGCTGAAGGCTCCATGCCCATG    3360

GCTGGAGCTGGGACCCTACACTTCTATAGTCAAGGTGCTTAGCCTCAAGGTTGCAGATGCACCCTCTAGTACTCTGGGTG    3440

CAGACTGTACACTGGGCGCAGGGGGTTGTGGAAGGACAGTGCAGATGATTCTGGGCTTTTGACACCACAGTTCCCCCAGG    3520

GAAAGAGGCACTACTAATAAAAACACTGACAGaaatctcctggtcaagtctgttaggcagcagagctcgaattc          3594
```

FIGURE 2 - cont.

MURINE α (1,3) FUCOSYLTRANSFERASE FUC-TVII, DNA ENCODING THE SAME, METHOD FOR PREPARING THE SAME, ANTIBODIES RECOGNIZING THE SAME, IMMUNOASSAYS FOR DETECTING THE SAME, PLASMIDS CONTAINING SUCH DNA, AND CELLS CONTAINING SUCH A PLASMID

BACKGROUND OF THE INVENTION

1. Field of the Invention

The present invention relates to murine α(1,3)fucosyltransferases, Fuc-TVII, DNA encoding such a murine α(1,3) fucosyltransferase Fuc-TVII, plasmids containing such DNA, cells transformed with such a plasmid, a method for producing a murine α(1,3)fucosyltransferase Fuc-TVII by culturing such cells, monoclonal antibodies which specifically bind to a murine α(1,3)fucosyltransferase Fuc-TVII, and immunoassays for detecting a murine α(1,3)fucosyltransferase Fuc-TVII using such monoclonal antibodies.

2. Discussion of the Background

Cell adhesion events between leukocytes and endothelial cells operate to facilitate the exit of blood leukocytes from the vascular tree. The selectin family of cell adhesion molecules, and their counter-receptors, function early in this process, mediating transient adhesive contacts between leukocytes and the endothelial cell monolayer. These selectin-dependent adhesive contacts, together with shear forces impinging upon the leukocyte, cause the leukocyte to "roll" along the endothelial monolayer. Leukocyte rolling, in turn, facilitates subsequent events that include leukocyte activation, firm leukocyte-endothelial cell attachment, and transendothelial migration (T. A. Springer, *Cell*, vol. 76, pp. 301-314 (1994); R. P. McEver et al, *J. Biol. Chem.*, vol. 270, pp. 11025-11028 (1995)).

E- and P-selectin, expressed by activated vascular endothelial cells, recognize glycoprotein counter-receptors displayed by leukocytes. Each of these selectins can operate to mediate leukocyte rolling in the context of inflammation. L-selectin has also been implicated in mediating leukocyte adhesion to activated vascular endothelium, through interactions with an as yet poorly understood endothelial cell ligand (M. L. Arbones et al, *Immunity*, vol. 1, pp. 247-260 (1994); K. Ley et al, *J. Exp. Med.*, vol. 181, pp. 669-675 (1995)). By contrast, lymphocyte L-selectin recognizes glycoprotein counter-receptors displayed by specialized cuboidal endothelial cells that line high endothelial venules (HEV) within lymph nodes and Peyer's patches. L-selectin-dependent adhesive interactions in this context operate to facilitate trafficking of lymphocytes (lymphocyte "homing") to such lymphoid aggregates.

The $NH_2$-terminal C-type mammalian lectin domain common to each of the three selectin family members mediates cell adhesion through calcium dependent interactions with specific oligosaccharide ligands, displayed by leukocytes (E- and P-selectin ligands) (R. P. McEver et al, *J. Biol. Chem.*, vol. 270, pp. 11025-11028 (1995); A. Varki, *Proc. Natl. Acad. Sci. U.S.A.*, vol. 91, pp. 7390-7397 (1994)), or by HEV (L-selectin) (S. D. Rosen et al, *Curr. Opin. Cell Biol.*, vol. 6, pp. 663-673 (1994)). Physiological ligand activity for E- and P-selectins is critically dependent on the expression of a non-reducing terminal tetrasaccharide termed sialyl Lewis x ($sLe^x$) [NeuNAcα2,3Galβ1,4(Fucα1,3)GlcNAc-R] (A. Varki, *Proc. Natl. Acad. Sci. U.S.A.*, vol. 91, pp. 7390-7397 (1994)), and/or its difucosylated variant (T. P. Patel et al, *Biochemistry*, vol. 33, pp. 14815-14824 (1994)). However, E- and P-selectins recognize this oligosaccharide in different contexts. P-selectin-dependent cell adhesion is optimal when $sLe^x$ is displayed by serine and threonine-linked oligosaccharides residing on a specific protein termed P-selectin glycoprotein ligand 1(PSGL-1) (K. L. Moore et al, *J. Cell. Biol.*, vol. 188, pp. 445-456 (1992); D. Sako et al, *Cell, vol.* 75, pp. 1179-1186 (1993)). $sLe^x$-modified PSGL-1 also appears to represent a high affinity counter-receptor for E-selectin (D. Asa et al, *J. Biol. Chem.*, vol. 270, pp. 11662-11670 (1995); K. D. Patel et al, *J. Clin. Invest.*, vol. 96, pp. 1887-1896 (1995)). A distinct leukocyte glycoprotein termed E-selectin ligand 1 (ESL-1) (M. Steegmaler et al, *Nature*, vol. 373, pp. 615-620 (1995)), and its α(1,3)fucosylated, asparagine-linked oligosaccharides, may also function as an E-selectin counter-receptor.

Physiological L-selectin counter-receptors on HEV are represented by the glycoproteins, GlyCAM-1 (L. A. Lasky et al, *Cell*, vol. 69, pp. 927-938 (1992)), CD34 (S. Baumhueter et al, *Science*, vol. 262, pp. 436-438 (1993)), and MadCAM-1 (E. L. Berg et al, *Nature*, vol. 366, pp. 695-698 (1993)). Biochemical studies indicate that L-selectin ligand activity of these molecules is also critically dependent upon post-translational modification by glycosylation. Early studies documented a requirement for sialylation and sulfation (Y. Imai et al, *J. Cell Biol.*, vol. 113, pp. 1213-1221 (1991)), implied a requirement for α(1,3)fucosylation, and indicated that these modifications are components of serine and/or threonine-linked glycans. More recent oligosaccharide structural analyses extend this work, and imply that high affinity L-selectin ligand activity depends upon the sulfated variant of the $sLe^x$ determinant, NeuNAcα2,3($SO_4$6)Galβ1,4(Fucα1,3)GlcNAc-R (S. Hemmerich et al, *Biochemistry*, vol. 33, pp. 4820-4829 (1994); S. Hemmerich et al, *Biochemistry*, vol. 33, pp. 4830-4835 (1994); S. Hemmerich et al, *J. Biol. Chem.*, vol. 270, pp. 12035-12047 (1995)).

Expression of $sLe^x$ is determined by cell lineage-specific expression of one or more α(1,3)fucosyltransferases (S. Natsuka et al, *Curr. Opin. Struc. Biol.*, vol. 4, pp. 683-691 (1994)). These enzymes utilize the donor substrate GDP-fucose, and catalyze a transglycosylation reaction involving the addition of α1,3-linked fucose to a common 3'-sialyl-N-acetyl-lactosamine precursor. It can be presumed that expression of the sulfated variant of $sLe^x$ also depends upon lineage-specific expression of α(1,3)fucosyltransferase activities operating on sulfate-modified 3'-sialyl-N-acetyl-lactosamine precursors, or that create $sLe^x$ moieties modified subsequently by sulfation.

The identity of the α(1,3)fucosyltransferase(s) responsible for selectin ligand expression in leukocytes is not well-defined, and HEV-specific α(1,3)fucosyltransferases have not been described. To date, five different human α(1,3)fucosyltransferases have been cloned (J. F. Kukowska-Latallo et al, *Genes & Dev.*, vol. 4, pp. 1288-1303 (1990); B. W. Weston et al, *J. Biol. Chem.*, vol. 267, pp. 24575-24584 (1992); B. W. Weston et al., *J. Biol. Chem.*, vol. 267, pp. 4152-4160 (1992); J. B. Lowe et al, *J. Biol. Chem.*, vol. 266, pp. 17467-17477 (1991); S. E. Goelz et al, *Cell*, vol. 63, pp. 1349-1356 (1990); R. Kumar et al, *J. Biol. Chem.*, vol. 266, pp. 21777-21783 (1991); S. Natsuka et al, *J. Biol. Chem.*, vol. 269, pp. 16789-16794 (1994); K. Sasaki et al, *J. Biol. Chem.*, vol. 269, pp. 14730-14737 (1994)). Northern blot and molecular cloning analyses imply that two of these, termed Fuc-TIV (J. B. Lowe et al, *J. Biol. Chem.*, vol. 266, pp. 17467-17477 (1991); S. E. Goelz et al, *Cell*, vol. 63, pp. 1349-1356 (1990); R. Kumar et al, *J. Biol. Chem.*, vol. 266, pp. 21777-21783 (1991)) and Fuc-TVII (S. Natsuka et al, *J. Biol. Chem.*, vol. 269, pp. 16789-16794 (1994); K. Sasaki et al, *J. Biol. Chem.*, vol. 269, pp. 14730-14737 (1994)), are expressed in leukocyte cells, and represent candidates for critical participation in selectin ligand expression. The role of Fuc-TIV (also known as ELAM-1 Ligand Fucosyl Transferase, or ELFT) in this process is not clear, however. While Fuc-TIV/ELFT is able to efficiently utilize non-sialylated N-acetyl-lactosamine precursors to direct expression of the $Le^x$ moiety (J. B. Lowe et al, *J. Biol. Chem.*, vol. 266, pp. 17467-17477 (1991); R. Kumar et al, *J. Biol. Chem.*, vol. 266, pp. 21777-21783 (1991)), this enzyme cannot determine $Le^x$ expression in all cellular contexts (S. Goelz et al, *J. Biol. Chem.*, vol. 269, pp. 1033-1040 (1994)), and its ability to do so in leukocytes, or in leukocyte progenitors, has not been demonstrated. By contrast, Fuc-TVII is apparently able to determine $sLe^x$ expression in all mammalian cellular contexts examined, where $sLe^x$ synthesis is biochemically possible (S. Natsuka et al, *J. Biol. Chem.*, vol. 269, pp. 16789-16794 (1994); K. Sasaki et al, *J. Biol. Chem.*, vol. 269, pp. 14730-14737 (1994)). Neither enzyme has been tested for its ability to participate in the synthesis of L-selectin ligands represented by the sulfated $sLe^x$ determinant.

Thus, there remains a need for additional α(1,3)fucosyltransferases and methods, cells, plasmids, and DNA useful for preparing the same. There also remains a need for antibodies and immunoassays useful for detecting such α(1,3) fucosyltransferases.

SUMMARY OF THE INVENTION

Accordingly, it is one object of the present invention to provide novel α(1,3)fucosyltransferases.

It is another object of the present invention to provide novel DNA encoding such a α(1,3)fucosyltransferase.

It is another object of the present invention to provide novel plasmids containing such DNA.

It is another object of the present invention to provide novel cells transformed with such a plasmid.

It is another object of the present invention to provide a novel method for preparing such an α(1,3)fucosyltransferase by culturing such a transformed cell.

It is another object of the present invention to provide novel monoclonal antibodies which bind specifically to such an α(1,3)fucosyltransferase.

It is another object of the present invention to provide a novel immunoassay for detecting such an α(1,3)fucosyltransferase using such a monoclonal antibody.

It is another object of the present invention to provide a novel method to fucosylate moieties by means of such an α(1,3)fucosyltransferase.

These and other objects, which will become apparent during the following detailed description, have been achieved by the inventors' cloning of α(1,3)fucosyltransferase Fuc-TVII.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 2 shows the nucleotide and deduced amino acid sequence of the isolated mouse Fuc-TVII gene. The DNA sequence was derived from a phage containing the murine Fuc-TVII locus. DNA sequence present in cDNAs (FIG. 1a) is shown in upper case, whereas DNA sequence corresponding to intronic positions is displayed in lower case. Amino acid sequences predicted by the cDNA sequences are shown in single letter code. As discussed in detail in the text, alternative splicing events yield different cDNAs that may in turn encode three different polypeptides. One protein is predicted to initiate at the methionine codon localized to nucleotide positions 996-998 (389 residues, 44,492 Da; cDNA 5; FIG. 1). A second protein is predicted to initiate at the methionine codon localized to nucleotide positions 1947-1949 (342 residues, 39,424 Da; cDNAs 6, 10, and 14; FIG. 1). The third protein is predicted to initiate at the methionine codon localized to nucleotide positions 2126-2128 (318 residues, 36,836 Da; cDNA 3, as well as all other cDNAs; FIG. 1);

FIG. 3a shows the polyadenylated RNA isolated from mouse tissues, and from the murine T-lymphocyte cell line 14-7fd (14FD).

FIG. 5a shows the co-localized expression of Fuc-TVII, MECA-79, and L-selectin ligands in HEV. Sequential 10 micron-thick frozen sections of axillary lymph nodes (column labeled Peripheral Lymph Node), mesenteric lymph nodes (column labeled Mesenteric Lymph Node), and Peyer's patches (column labeled Peyer's Patches) were stained with an antigen affinity purified rabbit polyclonal anti-murine Fuc-TVII (row labeled Fuc-TVII), with the monoclonal antibody MECA-79 (row labeled MECA-79), with a murine L-selectin/human IgM chimera (row labeled L-sel/IgM Chimera), or with the L-selectin/IgM chimera stained in the presence of EDTA (row labeled L-sel/IgM Chimera+EDTA). Detection of section-bound primary immunohistochemical reagents was subsequently accomplished using secondary immunochemical reagents labeled with flurochromes (FITC-conjugated [green] anti-rabbit IgG for Fuc-TVII; FITC-conjugated [green] anti-human IgM for L-selectin/IgM; rhodamine-conjugated [red] anti-rat IgM for MECA-79), as described in the Experimental Procedures in the Examples. These colored detection schemes yield white area on the black and white reproductions of the original photographs of these experiments. Thus, the "green" and "red" regions appear as white regions. Photomicrographs were taken at 40× magnification, using fluorescent microscopic procedures as described in the Experimental Procedures in the Examples.

DETAILED DESCRIPTION OF THE PREFERRED EMBODIMENTS

Figure 1A:
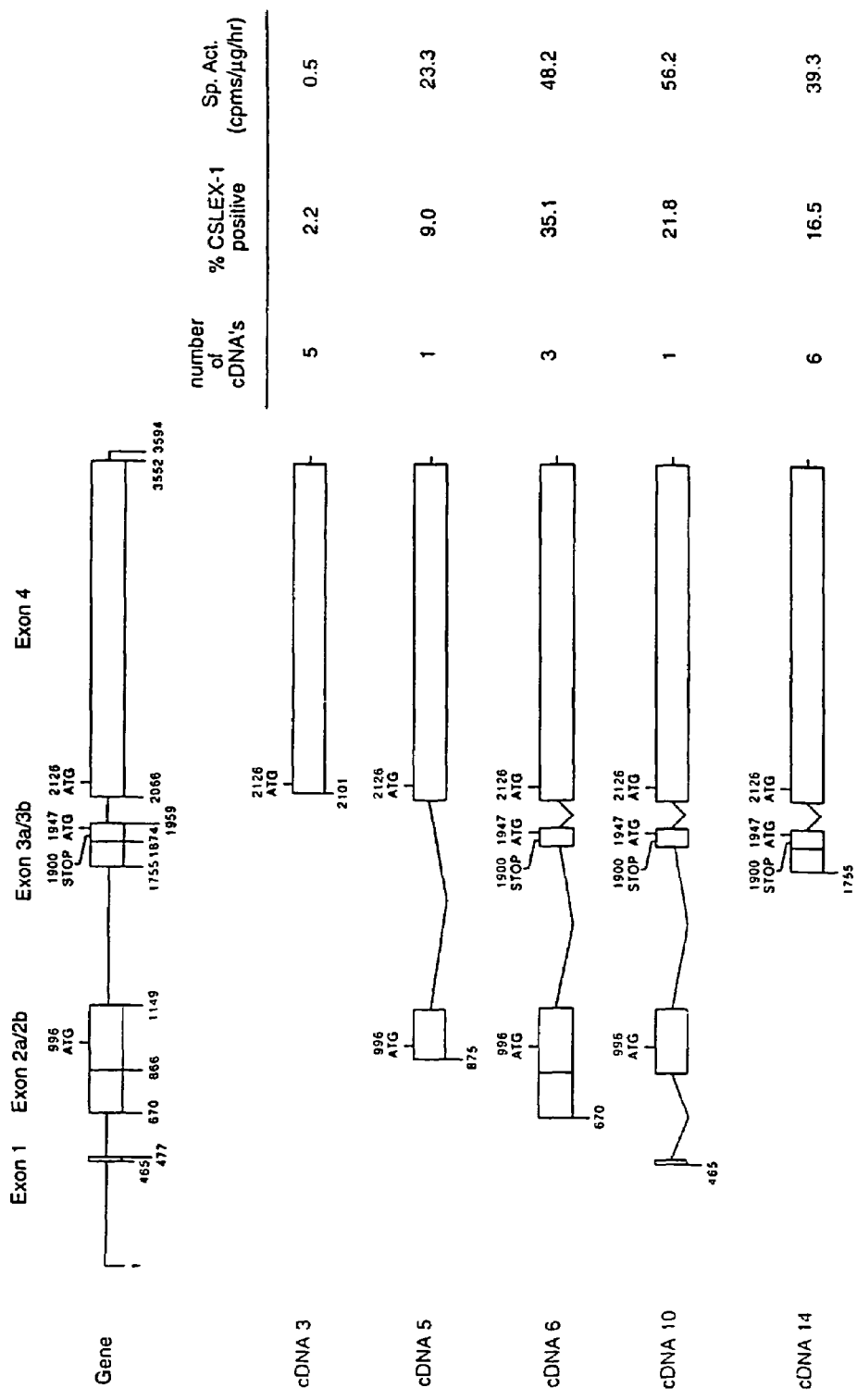
FIG. 1a shows the structure and functional activities of the murine Fuc-TVII gene and cDNAs. The multi-exon structure of the murine Fuc-TVII gene is shown at top. Numbering below the schematic corresponds to the nucleotide positions of intron-exon boundaries, and the first (1) and last (3520) nucleotides of the known sequence of the locus. Intron-exon boundaries are defined by comparison of the cDNA sequences to the corresponding genomic DNA sequence (see FIG. 2). Numbering above the schematic, immediately above "ATG"s, corresponds to the nucleotide position of the first nucleotide in each of the three potential initiation codons, as discussed in detail below. Numbering above the schematic, immediately above "STOP"s, corresponds to the nucleotide position of the translational termination codon (TGA; base pairs 1900-1902) localized to exon 3b, that truncates the potential open reading frame initiated by the start codon at nucleotide 996-998 in cDNA classes represented by cDNAs 6 and 10 (see text for details). Representative members of the five structurally different classes of Fuc-TVII cDNAs isolated from the murine cytotoxic T-lymphocyte cell line 14-7fd are schematically represented below the gene structure schematic. The cDNAs shown are the representative member of each class with the longest 5' extension. The number of cDNAs isolated in each class is indicated in the column labeled "number of cDNAs". Each cDNA was transiently expressed in COS-7 cells (see the Experimental Procedures in the Examples). The transfected COS-7 cells were then subjected to flow cytometry analysis to characterize the cell surface glycosylation phenotype determined by each cDNA. The fraction of sialyl Lewis x-positive cells in the transfected population (positive staining with the monoclonal antibody CSLEX-1) normalized to transfection efficiency as determined by chloramphenicol acetyl transferase activity encoded by a co-transfected plasmid vector encoding this enzyme (see the Experimental. Procedures in the Examples) is indicated in the column labeled "% CSLEX-1 positive". These results represent the fraction of antigen-positive cells observed above a background of 2% staining obtained with the negative control vector pCDM8. Extracts were also prepared from the transfected cells, and were subjected to in vitro α(1,3)fucosyltransferase assays using 5 mM sialyl-N-acetyl-lactosamine as an acceptor (see the Experimental Procedures in the Examples). The specific activity of the α(1,3)fucosyltransferase activity encoded by each cDNA (normalized for transfection efficiency) is indicated in the column labeled "Sp. Act. (cpms/µg/hr)".

Thus, in a first embodiment, the present invention provides novel enzymes, murine α(1,3)fucosyltransferases, murine Fuc-TVIIs. Suitably, the enzyme has one of the two amino acid sequences corresponding to the polypeptide encoded by the gene shown in FIG. 1a using one of two different ATG initiation codons. Thus, in a first embodiment, the present enzyme has the amino acid sequence corresponding to that encoded by the DNA corresponding to cDNA 5 in FIG. 1 and nucleotide positions 996 to 1149, and 2067 to 3079 in FIG. 2. In another embodiment, the enzyme has an amino acid sequence corresponding to that encoded by the cDNAs 6, 10, or 14 in FIG. 1 and having a nucleotide sequence corresponding nucleotide positions 1947 to 1959, and 2067 to 3079 shown in FIG. 2. In these two embodiments, it is to be understood that the amino acid sequences correspond to:

(1) that obtained by linking the C terminus of the amino acid sequence encoded by nucleotide positions 996 to 1149 of FIG. 2 to the N terminus of the amino acid sequence encoded by nucleotide positions 2067 to 3079 of FIG. 2; and (2) that obtained by linking the C terminus of the amino acid sequence encoded by nucleotide positions 1947 to 1959 of FIG. 2 to the N terminus of the amino acid sequence encoded by nucleotide positions 2067 to 3079 of FIG. 2.

The present enzyme may also have one of the amino acid sequences described above and in which up to 5 amino acid sequences have been added, deleted, or substituted at the amino terminus of the protein, provided that the enzyme retains its activity. In this context an enzyme is considered to retain its activity if it retains at least 10%, preferably at least ½, more preferably at least ½, of the specific activity of the native enzyme to transfer fucose from GDP-fucose to 3'-sialyl-N-acetyllactosamine as described in the examples below.

The present invention also provides novel fusion proteins in which any of the enzymes of the present invention are fused to a polypeptide such as protein A, streptavidin, fragments of c-myc, maltose binding protein, IgG, IgM, amino acid tag, etc. Preferably, the polypeptide fused to the present invention is fused to the amino terminus of the present enzyme. In addition, it is preferred that the polypeptide fused to the enzyme of the present invention is chosen to facilitate the release of the fusion protein from a prokaryotic cell or a eukaryotic cell, into the culture medium, and to enable its (affinity) purification and possibly immobilization on a solid phase matrix.

Examples of such fusion proteins include those in which the polypeptide, e.g., protein A, is fused to the glycine residue encoded by nucleotide positions 2067 to 2069 in FIG. 2 or to the amino group of the proline residue encoded by nucleotide positions 2162 to 2164 in FIG. 2.

In another embodiment, the present invention provides novel DNA sequences which encode murine Fuc-TVII, or a fusion protein according to the present invention. Suitably, the present DNA sequence is any which encodes the two amino acid sequences described above. Thus, in a first embodiment, the DNA sequence is any encoding a polypeptide having the amino acid sequence corresponding to that encoded by the cDNA 5 in FIG. 1 and having the sequence corresponding to nucleotide positions 996 to 1149, and 2067 to 3079 in FIG. 2. In another embodiment, the DNA sequence is any which encodes a protein having the sequence corresponding to that encoded by the cDNAs 6, 10, or 14 in FIG. 1 and having the sequence corresponding to nucleotide positions 1947 to 1959, and 2067 to 3079 shown in FIG. 2.

Of course, the DNA sequence may encode a protein which corresponds to any of those described above but in which up to 5 amino acid residues have been added, deleted, or substituted at the amino terminus of the protein, provided that the protein retains its activity. In addition, the DNA sequence may encode any of the present fusion proteins.

In a preferred embodiment, the DNA sequence has the nucleotide sequence corresponding to from position 996 to 1149, and 2067 to 3079 shown in FIG. 2. In another preferred embodiment, the DNA sequence has the nucleotide sequence corresponding to from position 1947 to 1959, and 2067 to 3079 in the nucleotide sequence shown in FIG. 2.

In these preferred DNA sequences, it is to be understood that the DNA sequence is:

(1) that obtained by linking the 3' terminus of the sequence corresponding to nucleotide positions 996 to 1149 in FIG. 2 to the 5' terminus of the sequence corresponding to nucleotide positions 2067 to 3079 in FIG. 2; and (2) that obtained by linking the 3' terminus of the sequence corresponding to nucleotide positions 1947 to 1959 in FIG. 2 to the 5' terminus of the sequence corresponding to nucleotide positions 2067 to 3079 in FIG. 2.

Another set of preferred DNA sequences includes the DNA having a sequence corresponding to nucleotide positions 996 to 3079 in FIG. 2 and the DNA having a sequence corresponding to nucleotide positions 1947 to 3079 in FIG. 2.

The cloning of the full length DNA sequence shown in FIG. 2 is described in great detail in the Examples below. The shorter length fragments of this sequence as well as the other DNA sequences of the present invention may be obtained by conventional techniques, such as solid state DNA synthesis or site-directed mutagenesis (Maniatis, T., et al, Molecular Cloning: A Laboratory Manual, Cold Spring Harbor Press, Cold Spring Harbor, N.Y. (1989) and Ausebel, F. M., et al, Current Protocols in Molecular Biology, John Wiley & Sons, NY (1989)).

In yet another embodiment, the present invention provides novel plasmids or vectors which contain a DNA sequence according to the present invention. The present plasmid may be either a cloning vector or an expression plasmid. Suitable plasmids or vectors are those obtained by inserting a DNA sequence of the present invention into a plasmid or vector such as pCDM8, pcDNA1, pREP8, pCEP4, PTZ18, etc. In the case of an expression plasmid, the DNA sequence of the present invention is preferably inserted into the plasmid downstream from a promoter and in the correct reading frame and transcriptional orientation. The insertion of a DNA sequence according to the present invention into any conventional expression plasmid in the correct reading frame and transcriptional orientation and the insertion of a DNA sequence of the present invention into a conventional cloning vector can easily be accomplished by the skilled artisan using conventional recombinant DNA technology.

The present invention also provides transformed cells which contain a plasmid or vector according to the present invention. Suitable host cells include any mammalian cell. Preferred host cells include Chinese hamster ovary cells, COS cells, etc. The transformation of such host cells with a plasmid or vector according to the present invention may be carried out using conventional techniques Ausebel, F. M., et al, Current Protocols in Molecular Biology, John Wiley & Sons, NY (1989).

In a further embodiment, the present invention provides a method for producing an enzyme of the present invention by culturing in a culture medium a transformed cell according to the present invention for a time sufficient to produce the enzyme. Preferably, the cell has been transformed with an expression plasmid such as cDNA5, cDNA6, cDNA10, or cDNA 14, shown in FIG. 1a, into which one embodiment of the present DNA has been inserted. The particular culture conditions, such as temperature, medium, etc., will depend on the type and identity of the transformed cell. However, the selection of appropriate conditions is well within the abilities of the skilled artisan. For example, suitable culture conditions and media for a variety of cell types are taught in Ausebel, F. M., et al, Current Protocols in Molecular Biology, John Wiley & Sons, NY (1989), which is incorporated herein by reference.

In another embodiment, the present invention provides novel monoclonal or polyclonal antibodies which specifically bind to the present enzymes. Such antibodies may be produced using conventional methods such as described in Harlow, E. et al, Antibodies: A Laboratory Manual, Cold Spring Harbor Laboratory Press, Cold Spring Harbor, N.Y. (1988), which is incorporated herein by reference. Preferably, the present antibodies are monoclonal antibodies. The present antibodies may be labelled with any conventional label, such as a radiolabel, a chromophore (e.g., a fluorescent label), or an enzyme (e.g., horseradish peroxidase).

The present invention also provides novel immunoassays for the detection and/or quantitation of the present enzymes in a sample. The present immunoassays utilize one or more of the present monoclonal or polyclonal antibodies which specifically bind to the present enzymes. Preferably the present immunoassays utilize a monoclonal antibody. The present immunoassay may be a competitive assay, a sandwich assay, or a displacement assay, such as those described in Harlow, E. et al, Antibodies. A Laboratory Manual, Cold Spring Harbor Laboratory Press, Cold Spring Harbor, N.Y. (1988) and may rely on the signal generated by a radiolabel, a chromophore, or an enzyme, such as horseradish-peroxidase.

The DNA sequences, enzymes, plasmids, cells, and methods of the present invention have a number of uses. Thus, the present invention provides previously undiscovered murine DNA sequences that encode specific and heretofore undiscovered protein sequences capable of functioning as a GDP-Fuc:NeuNAcα(2,3)-β-D-Gal(1,4)-D-GlcNAc α(1,3)-fucosyltransferase. These enzymes, when expressed by the present DNA sequence, function within mammalian cells to generate de novo expression of specific cell surface glycoconjugate structures on those cells. These structures are recognized by an antibody against the sialyl Lewis x determinant {NeuAcα(2,3)Galβ(1,4)[Fucα(1,3)]GlcNAc-R}, where R is an underlying glycoconjugate-glycoprotein, glycolipid, free oligosaccharide, or hydroxyl group. It has been demonstrated that these enzymes do not generate de novo expression of specific cell surface glycoconjugate structures known as the stage specific embryonic antigen I (SSEA-1 or Lewis x; structure Galβ(1,4)[Fuc α(1,3)]GlcNAc), the Lewis a structure, or the sialyl Lewis a structure. This enzyme, when expressed by the cloned DNA sequence described here, has also been shown to function in the enzymatic manner implied in its name, when assayed in extracts prepared from cells that express the DNA sequence. The oligosaccharide products of this enzyme represent fucose linked in alpha 1,3 configuration to the GlcNAc residue of an α(2,3)sialylated "type II" lactosamine acceptor. This product is hereinafter referred to as the sialyl Lewis x determinant. For convenience, this reaction is shown in the equation given below:

The location of the catalytic domain of the present enzyme is inferred by comparison to the catalytic domain of several structurally similar enzymes. Specific utilities include:

i. Construction of Animal Cell Lines with Specific Capabilities with Respect to Post-Translational Modification of the Oligosaccharides on Cell-Surface, Intracellular, or Secreted Proteins or Lipids by Sialyl Lewis X Determinants that Represent the Products of this Enzyme (for the Production of Diagnostics and Therapeutics by the Biotechnology Industry).

Specifically, the cloned DNA sequences described here may be introduced by standard technologies into a mammalian cell line that does not normally express the cognate enzyme or its product (sialyl Lewis x determinants on oligosaccharides), but which does maintain expression of the appropriate oligosaccharide precursors(s), and GDP-fucose, and transcribed in that cell in the "sense" direction, to yield a cell line capable of expressing sialyl Lewis x determinants on oligosaccharides on cell-surface, intracellular, or secreted proteins or lipids. Alternatively, these cloned DNA sequences may be introduced by standard technologies into a mammalian cell line that does express the cognate enzyme and its product (sialyl Lewis x determinants), and transcribed in that cell in the "anti-sense" direction, to yield a cell line incapable of expressing sialyl Lewis x determinants on cell-surface, intracellular, or secreted proteins or lipids. The introduction and "anti-sense" transcription of the present DNA sequences in a cell may be carried out using conventional methods as described in Maniatis, T., et al, Molecular Cloning: A Laboratory Manual, Cold Spring Harbor Laboratory Press, Cold Spring Harbor, N.Y. (1989), which is incorporated herein by reference. Alternatively, the endogenous GDP-Fuc:NeuNAcα(2,3)-β-D-Gal(1,4)-D-GlcNAc α(1,3)fucosyltrans-

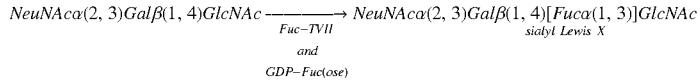

$$NeuNAc\alpha(2,3)Gal\beta(1,4)GlcNAc \xrightarrow[\text{and}]{\text{Fuc-TVII}} NeuNAc\alpha(2,3)Gal\beta(1,4)[Fuc\alpha(1,3)]GlcNAc$$
$$GDP-Fuc(ose) \quad \text{sialyl Lewis X}$$

The transfer of GDP-fucose to NeuNAcα(2,3)Galβ[SO₄-6]GlcNAc proceeds analogously.

This enzyme may also be able to utilize other oligosaccharide precursors similar or identical to those shown below, wherein the underlined Gal or GalNAc moiety is substituted with another molecule (mono- or oligosaccharide, a modified sialic acid moiety, or sulfate, for example) and transfer fucose in α(1,3)linkage to the GlcNAc residues on these molecules also referred to hereinafter as sialyl Lewis X for simplicity's sake:

Galα(1,3)Galβ(1,4)GlcNAc-R

NeuNAcα(2,3)[GalNAcβ(1,4)]Galβ(1,4)GlcNAc-R

NeuNAcα(2,3)GalNAcβ(1,4)GlcNAc-R

N-glycolylNeuα(2,3)Galβ(1,4)GlcNAc-R

SO₄-3-Galβ(1,4)GlcNAc-R

NeuNAcα(2,3)[SO₄-6]Galβ(1,4)GlcNAc-R

NeuNAcα(2,3)[SO₄-6]Galβ(1,4)[SO₄-6]GlcNAc-R wherein R is a N-linked or O-linked oligosaccharide moiety or backbone.

ferase gene(s), in a mammalian cell expressing the cognate enzyme(s), might be inactivated with the present DNA sequence by homologous recombination techniques, or by "anti-sense" oligonucleotide approaches using the present DNA sequences, or by dominant negative mutant fucosyltransferase sequences that inactivate endogenous GDP-Fuc:NeuNAcα(2,3)-β-D-Gal(1,4)-D-GlcNAc α(1,3)-fucosyltransferase(s), derived via mutagenesis and genetic selection schemes, from the present DNA sequences, or from structurally related but otherwise wild type α(1,3)fucosyltransferases.

This method may be used to construct animal cell lines that are suitable host cells for the production of diagnostic or therapeutic materials whose usefulness or efficacy depends upon the specific post-translational modification determined by the present cloned DNA sequences and their cognate enzymes. For example, it is known that the biological effectiveness of many therapeutic proteins or peptides, recombinant or otherwise, depends critically upon the oligosaccharide structure(s) that are covalently attached to them. The structure of these oligosaccharides is primarily a function of the number and kind of glycosyltransferase enzymes that are found in the cell used to produce these therapeutic products. Animal cells and some yeasts are competent to perform these glycosylation reactions; however, not all glycosyltransferase enzymes are produced by every animal cell or yeast, and therefore, some oligosaccharide structures (including sialyl Lewis x determinants generated by the present enzyme) are not produced by them. The converse is also true, namely, that producing cells may express a glycosyltransferase analogous to, or identical to, the GDP-Fuc:NeuNAcα(2,3)-β-D-Gal(1,4)-D-GlcNAc α(1,3)-fucosyltransferase encoded by the DNA sequence described here. It is likely that sialyl Lewis x determinants may alter the bioactivity (for better or for worse) of natural or recombinant therapeutic or diagnostic agents (glycoproteins or glycolipids) produced by mammalian or other eukaryotic hosts. Eukaryotic host cells that the biotechnology industry uses to produce these recombinant agents may be altered with the DNA sequence information and related information described in this invention, to add sialyl Lewis x determinants to the oligosaccharides on recombinant products by expressing all or part of the cloned sequences described here in the desired host. Alternatively, sialyl Lewis x determinants may be eliminated from the product produced in these host cells by the use of transfected "anti-sense" vector constructs, recombination-based gene inactivation, "anti-sense" oligonucleotide approaches, or dominant negative mutant fucosyltransferases, outlined above.

The old "methods" used for this process include an empirical approach to identify a cell line that does or does not express this particular enzyme or an enzyme that functions in a similar or identical manner, for the production of the appropriately modified recombinant or natural product. This is not always optimal since cell lines with this particular post-translation modification capabilities may not exist naturally, or may not be especially suited to high level production of an appropriately modified product. Alternatively, unwanted sialyl Lewis x determinants present on a therapeutic material produced by an empirically identified animal cell line must be removed chemically or enzymatically, a process that may be costly or inefficient. The advantages of using the cloned, functional present DNA sequences in conjunction with the technologies outlined above, relative to these older methods include the ability to construct lines that specifically lack the capability to generate sialyl Lewis x determinants on the oligosaccharides of glycoproteins or glycolipids. Properly constructed, these cell lines will eliminate any need for chemical or enzymatic treatment of a therapeutic or diagnostic material to remove unwanted sialyl Lewis x determinants. Moreover, in the event that sialyl Lewis x determinants are found to be desirable for a particular diagnostic or therapeutic product produced by animal cells, cell lines may be engineered with the present cloned DNA sequence to generate these residues.

ii. Isolation of Reagents Suitable for Efficient Enzymatic Synthesis and Production of Oligosaccharides (in Enzyme Reactors, for Example).

Oligosaccharides may have therapeutic utility as immunomodulatory reagents in the field of organ transplantation. In particular, soluble and solid-phase oligosaccharides may find use as therapeutic agents with which to block or ameliorate antibody-mediated organ transplant rejection in cases involving incompatibility due to differences in the major blood group antigen systems of the organ donor and the recipient, including the Lewis blood group system. Likewise, soluble oligosaccharides may find use as therapeutic agents that function by blocking attachment of bacterial, viral, or parasitic pathogens to glycoconjugate "receptors" found on the surface of the animal tissues that these pathogens invade. For example, there is evidence that portions of the Lewis blood group oligosaccharide antigens serve as "receptors" for some forms of uropathogenic bacteria. Moreover, such glycoconjugates have been implicated in modulating adhesive events between cells, and between cells and their environment during developmental and differentiation processes. These events include binding of spermatozoa to eggs, and the initial events that mediate attachment of fertilized ova to the uterine wall at the beginning of implantation. These observations suggest, for example, the possibility that contraceptive uses for (biologically "natural") oligosaccharide molecules might exist. In addition, specific glycoconjugates containing sialyl Lewis x determinants have been implicated as ligands for the Selectin family of adhesion molecules, that play important roles in mediating adhesion between cells of the immune system, and some tumor cells, and the surfaces of the endothelial cells that lin the vascular tree. Published observations confirm that the cloned fucosyltransferase sequence described here could be used to construct oligosaccharide-type molecules, with pharmaceutical properties possessing anti-inflammatory and anti-tumor metastatic functions, and that can prevent life-threatening tissue damage in acute lung disease (ARDS) and in tissue re-perfusion, after myocardial infarction, for example (see, e.g., Buerke, M., et al, *J. Clin. Invest.*, vol. 93, pp. 1140-1148 (1994); Mulligan, M. S., et al, *Nature*, vol. 364, pp. 149-151 (1993); and Mulligan, M. S., et al, *J. Exp. Med.*, vol. 178, pp. 623-631 (1993)).

Currently, pharmaceutically useful amounts of oligosaccharides containing sialyl Lewis x determinants are produced by chemical synthesis (a procedure that is inefficient and costly), by isolation from natural sources (using costly and inefficient procedures that often require the processing of large quantities of animal or plant material, and the purification of the desired oligosaccharide from other contaminating oligosaccharides), or by glycosyltransferase-assisted synthetic procedures, using other recombinant α-(1,3)fucosyltransferases. The invention described here provides a mechanism to synthesize abundant quantities of purified GDP-Fuc: NeuNAcα(2,3)-β-D-Gal(1,4)-D-GlcNAc α(1,3)-fucosyltransferase. This could be used to construct an enzyme bioreactor (enzyme in solution or immobilized on a solid phase matrix, for example via the protein-A moiety fused to the catalytic domain of the enzyme, as described in Ball, et al, *J. Am. Chem. Soc.*, vol. 114, pp. 5449-5451 (1992) capable of enzymatic synthesis of structures containing sialyl Lewis x determinants. This may be more efficient than approaches involving chemical synthesis of structures containing sialyl Lewis x determinants or their purification from natural sources, or by using other known α(1,3)fucosyltransferases, for a variety of reasons. One, the only chemicals necessary would be the enzyme substrates; these are easily obtained or synthesized. Two, enzymatic synthesis of such structures will produce only the desired product and the nucleotide diphosphate product of substrate hydrolysis. This latter chemical is found as the natural by-product of these reactions in animal cells, is relatively non-toxic, and may be easily separated from the oligosaccharide synthetic product. By contrast, chemical synthetic procedures typically generate numerous products of side reactions which must be removed, and which may be toxic as well. Similarly, purification of oligosaccharides from natural sources requires the removal of other contaminating oligosaccharides present in the natural material. Three, enzymatic catalysis is extraordinarily efficient; nearly complete conversion of substrate to product can be achieved. By contrast, chemical synthesis of sialyl Lewis x determinants on oligosaccharides is a multi-step process; yields at each step may be much less than 100%, and the cumulative efficiency of current chemical synthesis procedures does not approach the efficiency possible with enzymatic synthesis. Similarly, purification of oligosaccharides with sialyl Lewis x determinants from natural materials can entail significant losses inherent to the purification procedures required to separate the desired oligosaccharide from contaminating, irrelevant oligosaccharides, with inefficient isolation of the desired oligosaccharide. The GDPFuc:NeuNAcα(2,3)-β-D-Gal(1,4)-D-GlcNAc α(1,3)-fucosyltransferase encoded by the present DNA sequence has never been previously identified in animal tissues. In theory, however, this activity may be partially purified from animal tissues for synthetic use. These purifications are themselves typically inefficient, however, primarily because such enzymes are typically present in very low abundance. This invention provides two mechanisms that may provide for the abundant production of this enzyme. First, this may be done through the construction and selection of animal cells that produce relatively large quantities of the enzymes. Alternatively, present nucleic acid sequences may then be used with standard recombinant DNA technologies to produce large quantities of glycosyltransferases in mammalian host cells, fungi, yeasts, or using other eukaryotic cell-based systems (i.e. baculovirus mammalian host), or in prokaryotic hosts. Furthermore, the sequence encoding this enzyme may be modified via standard molecular cloning schemes or mutagenesis to yield a recombinant fucosyltransferase with novel properties that make it more desirable than the wild-type enzyme. For example, the modifications might be made to the enzyme that make it more stable, more suitable for immobilization in a bioreactor, or more catalytically efficient for a particular substrate.

iii. Isolation of Reagents Suitable for Producing Recombinant GDP-Fuc:NeuNAcα(2,3)-β-D-Gal(1,4)-D-GlcNAc α(1,3)fucosyltransferase to be Used Directly as a Research Reagent, or to be Used to Generate Antibodies Against the GDPFuc:NeuNAcα(2,3)-β-D-Gal(1,4)-D-GlcNAc α(1,3) fucosyltransferase, for Research Applications.

The present invention provides two methods for producing large quantities of the present enzymes (see ii, above—i.e. specially constructed animal cells, or via natural or synthetic genes encoding these enzymes) which may be used as a research tool with which to study the structures and functions of oligosaccharides and glycoproteins. Likewise, the enzymes produced by this method, or the nucleic acid sequences and derived protein sequences provided by this method, may be used to generate antibodies to this enzyme (via synthetic peptides or recombinant protein). These antibodies might also be used as research reagents to study the biosynthesis and processing of these enzymes, and might be used as an aid in their purification for all the uses described herein.

iv. Antibodies to Glycosyltransferases as Diagnostic Reagents.

Aberrant expression of α(1,3)fucosyltransferases has been associated with malignancy in humans, indicating that this enzyme may serve as a tumor marker for early detection of malignancy involving a number of human tissues. Enzyme tumor markers have typically been assayed in body fluids by activity assays, which may be subject to non-specificity due to competing glycosyltransferase activity. These assays may also be insensitive since it is possible that inactive enzymes might be useful as tumor markers but would not be detected by enzyme activity assays. This invention provides a mechanism for generating antibodies to this enzyme (monoclonal and polyclonal antibodies against synthetic peptides constructed from information derived from cloned DNA sequence encoding GDP-Fuc:NeuNAcα(2,3)-β-D-Gal(1,4)-D-GlcNAc α(1,3)fucosyltransferase, or against the recombinant enzyme produced by eukaryotic or prokaryotic hosts). Antibodies specific for this GDP-Fuc:NeuNAcα(2,3)-β-D-Gal(1,4)-D-GlcNAc α(1,3)-fucosyltransferase so produced may be used to detect and quantitate this glycosyltransferases in body fluids, with specificity and sensitivity exceeding enzyme activity assays, serving as a method for the early detection of malignancy.

v. Recombinant Enzyme for Use in Screening Natural and Synthetic Compounds for Fucosyltransferase Inhibitors or Inactivators.

It is known that the sialyl Lewis x determinant is an essential component of counterreceptors for the E-selectin and P-selectin. Related compounds are candidate ligands for L-selectin. These receptor-counter-receptor pairs operate to enable leukocytes (neutrophils, monocytes, eosinophils, lymphocytes in general (in recirculatary events), and some kinds of T lymphocytes) to leave the vascular tree and participate in normal inflammatory events in humans, or in pathological inflammatory events in humans (like ARDS, tissue-reperfusion injury, and a host of other such events). Since the present GDP-Fuc:NeuNAcα(2,3)-β-D-Gal(1,4)-D-GlcNAc α(1,3)-fucosyltransferase gene is expressed in human leukocytes and plays a central role in sialyl Lewis x biosynthesis, pharmacologic inhibitors of this enzyme will diminish leukocyte sialyl Lewis x expression and thus act as antiinflammatory pharmaceutical agents for use in humans or other animals in acute and chronic selectin-dependent inflammatory states. The GDP-Fuc:NeuNAcα(2,3)-β-D-Gal(1,4)-D-GlcNAc α(1,3)-fucosyltransferase described here represents a tool for identifying compounds that inhibit this enzyme, either through "screening" methods to identify such compounds in natural product or chemical libraries (using recombinant enzyme or cell lines expressing this enzyme, in screening assays), or through "rational drug design" strategies (via solution of the enzyme's tertiary structure with the aid of recombinant enzyme, followed by design or identification of molecules that inhibit the enzyme's catalytic activity or other essential function).

A number of studies have noted an association between increased numbers of cell surface sialyl Lewis x determinants on oligosaccharides of a cell and the ability of that cell to metastasize in a malignant fashion. If there is a causal relationship here, then drugs that inhibit the present enzyme may be used as anti-tumor agents. The reagents described in this disclosure may prove useful for screening compounds for antifucosyltransferase activity, since the cloned sequence may be used with standard techniques to produce relatively large amounts of pure fucosyltransferase. This will aid in screening since the effects of potential inhibitors will be tested on a pure enzyme, without the confounding effects that may occur in whole cell extracts or with partially purified enzyme.

vi. Engineering of Glycosyltransferase Substrate Specificity to Generate Novel Glycoconjugate Structures on Secreted or Cell-Associated Glycoconjugates.

The present invention provides a cloned GDP-Fuc:NeuNAcα(2,3)-β-D-Gal(1,4)-D-GlcNAc α(1,3)-fucosyltransferase gene that, when used with appropriate mutagenesis and genetic selection schemes, may allow the generation of mutant GDP-Fuc:NeuNAcα(2,3)-β-D-Gal(1,4)-DGlcNAc α(1,3)-fucosyltransferases that generate glycosidic linkages different from that generated by the wild-type enzyme. These novel linkages may or may not be naturally occurring, and could find utility as moieties that enhance bioactivity of the molecules to which they are attached. Directed mutagenesis procedure may also be considered since this enzyme maintains primary sequence similarity to other α(1,3)fucosyltransferases, yet exhibits a distinct set of acceptor substrate utilization properties. Alternatively, mutagenesis and selection approaches may be used to generate mutant GDP-Fuc: NeuNAcα(2,3)-β-D-Gal(1,4)-D-GlcNAc α(1,3)-fucosyltransferases that act in a dominant negative fashion. The dominant negative mutants so generated may be used to inactivate endogenous glycosyltransferase activities when the product(s) of such an enzyme are not desired. Mutant GDP-Fuc:NeuNAcα(2,3)-β-D-Gal-(1,4)-D-GlcNAc α(1,3)-fucosyltransferases may also be generated, for example, that function as fucosidases that hydrolyze various sugar linkages (fucose, mannose, or others) from oligosaccharides in vitro and in vivo.

vii. Genotyping Individuals at this Fucosyltransferase Locus.

Absence of a fucosyltransferase similar to the one encoded by the DNA sequence detailed here has been found in several families. Should such absence be associated with a detrimental phenotype, DNA sequence polymorphisms, including restriction fragment length polymorphisms, within or linked to the gene corresponding to this cloned gene segment may be used to genotype individuals at this locus, for the purpose of genetic counseling. Likewise, the molecular basis for such detrimental phenotypes might be elucidated via the study of the gene segment described here, should it be causally-related to such phenotypes.

viii. Identification and Production of Inhibitors that Operate as Anti-Inflammatory Pharmaceuticals.

Much effort is being exerted trying to identify compounds that will inhibit sialyl Lewis x formation in human white cells, since such molecules, if non-toxic, will act as antiinflammatory pharmaceuticals by preventing the synthesis of sialyl Lewis x in white cells, thus rendering the cells unable to bind to inflamed vascular endothelium (via selecting) during inflammation, and thus unable to participate in extravascular inflammatory activities. One candidate target for such molecules is the Fuc-TVII enzyme. This is a better candidate than any of the other known fucosyltransferases since it is the only known fucosyltransferase that is expressed in meaningful quantities in white cells and in high endothelial venules in lymphoid aggregates, that can also synthesize the sialyl Lewis x determinant. Furthermore, the leukocytes of mice genetically engineered for a deficiency in this enzyme are deficient in expression of functional ligands for E-selectin and P-selectin, and exhibit a concomitant immune deficiency characterized by a deficit in leukocyte mobilization to inflammatory sites. These observations demonstrate that Fuc-TVII controls leukocyte selectin ligand expression, and indicate that inhibition of this enzyme by pharmaceutical agents or maneuvers will represent an antiinflammatory approach that may have therapeutic benefit in human disease where selectin-dependent inflammation is pathologic. The availability of recombinant Fuc-TVII will facilitate identification of such inhibitory compounds since it may be used in high throughput assays to screen chemical libraries and natural product libraries for inhibitors. Moreover, the recombinant form of the enzyme, or a derivative of the enzyme made via recombinant techniques, may be used to determine its tertiary conformation, including the shape of functionally important surfaces (i.e. GDP-fucose binding pocket, metal binding pocket, oligosaccharide acceptor substrate binding pocket, etc.). One could then use "rational drug design" approaches to identify or synthesize molecules with morphological complementarity that act as inhibitors.

ix. A "One-Pot", In Vitro Synthesis of the Sialyl Lewis x Tetrasaccharide.

The sialyl Lewis x tetrasaccharide, and some derivatives, have been shown to operate as anti-inflammatory molecules in animal models of selectin-dependent inflammation (see, e.g., M. Buerke et al, *J. Clin. Invest.*, vol. 93, pp. 1140-1148 (1994); M. S. Mulligan et al, *Nature*, vol. 364, pp. 149-151 (1993); and M. S. Mulligan et al, *J. Exp. Med.*, vol. 178, pp. 623-631 (1993)). These molecules are now in clinical trials. Chemical synthesis of the sialyl Lewis x molecule is extremely expensive. Glycosyltransferase-assisted synthetic procedures have therefore been developed, in which recombinant glycosyltransferases are used to effect specific and efficient synthesis of the sialyl Lewis x moiety. These systems involve additional enzymes (not shown in the schemes below) that continuously form the nucleotide sugar substrates necessary to the glycosyltransferases (see Ichikawa et al, *J. Am. Chem. Soc.*, vol. 114, p. 9283 (1992). Because of the nature of the previously existing enzymes, the conventional synthetic scheme had to proceed in a "two-pot" synthesis (see below), where the sialyated product of the first pot would have to be separated from the non-sialylated intermediate product (of Rxn #1), and then added to a second "pot" where Rxn #3 could take place. This was necessary in order to avoid a competing reaction (Rxn#4), since the available fucosyltransferases (i.e Fuc-TIII, Fuc-TV, and Fuc-TVI) would transfer to Galβ(1,4)GlcNAc (to form Lewis x) and also to NeuNAcα(2,3)Galβ(1,4)GlcNAc (to form sialyl Lewis x). Since Lewis x cannot be sialylated by any known α(2,3)sialyltransferases (Rxn #5), the formation of Lewis x would effectively diminish the yield by depleting substrate for Rxn #2.

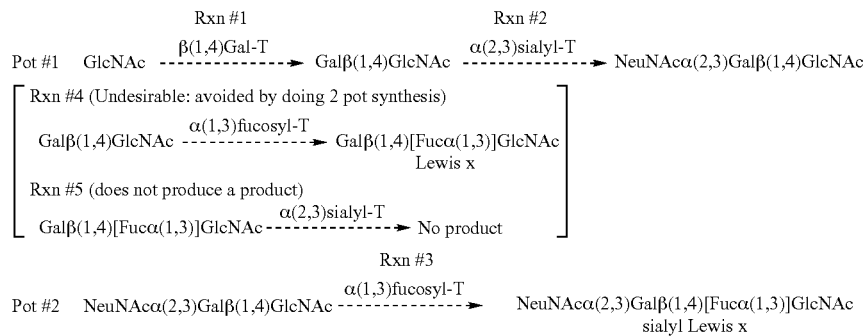

This problem can be circumvented with Fuc-TVII. This enzyme cannot operate on Galβ(1,4)GlcNAc, so it can be included in the first pot. It will not operate until the product of Rxn #2 is made, at which time it will complete rxn #3. Thus, Fuc-TVII makes possible the one-pot synthesis shown below:

One-Pot Synthesis

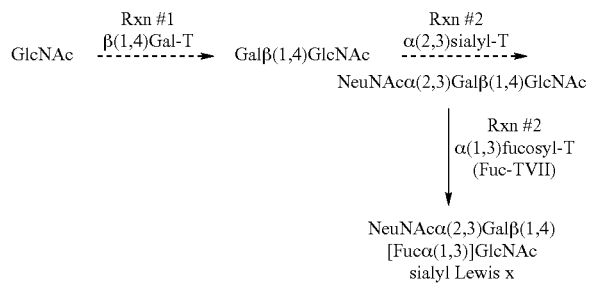

Other features of the invention will become apparent in the course of the following descriptions of exemplary embodiments which are given for illustration of the invention and are not intended to be limiting thereof.

EXAMPLES

Experimental Procedures

Cell Culture. The sources and growth conditions for COS-7 cells (K. M. Gersten et al, *J. Biol. Chem.*, vol. 270, pp. 25047-25056 (1995)), CHO-Tag cells (P. L. Smith et al, *J. Biol. Chem.*, vol. 269, pp. 15162-15171 (1994)), and cultured murine blood cell lines (B cell line S107, (M. L. Atchison et al, *Cell*, vol. 48, pp. 121-128 (1987)); T cell line EL4, (L. J. Old et al, *Cancer Res.*, vol. 25, pp. 813-819 (1965)); B cell hybridoma line TH2.54.63, (T. Hamano et al, *J. Immunol.*, vol. 130, pp. 2027-2032 (1983)); B cell hybridoma line 180.1, (M. Hummel et al, *J. Immunol.*, vol. 138, pp. 3539-3548 (1987)); Friend murine erythroleukemia cell line MEL, (D. Singer et al, *Proc. Natl. Acad. Sci. U.S.A.*; vol. 71, pp. 2668-2670 (1974); B. L. Weber et al, *Science*, vol. 249, pp. 1291-1293 (1990)); macrophage cell line RAW264.7, (P. Ralph et al, *J. Immunol.*, vol. 119, pp. 950-954 (1977); W. C. Raschke et al, *Cell*, vol. 15, pp. 261-267 (1978)); macrophage cell line P388D$_1$, (H. S. Koren et al, *J. Immunol.*, vol. 114, pp. 894-897 (1975)); and the cytotoxic T-cell line 14-7fd, (T. J. Braciale et al, *J. Exp. Med.*, vol. 153, pp. 910-923 (1981); M. E. Andrew et al, *J. Immunol.*, vol. 132, pp. 839-844 (1984)).

Antibodies. The sources of the monoclonal antibodies used her have been described previously (anti-Lewis x/anti-SSEA-1, (D. Solter et al, *Proc. Natl. Acad. Sci. U.S.A.*, vol. 75, pp. 5565-5569 (1978)); anti-H and anti-Lewis a, (K. M. Gersten et al, *J. Biol. Chem.*, vol. 270, pp. 25047-25056 (1995)); anti-sialyl Lewis x/CSLEX, (K. Fukushima et al, *Cancer Res.* vol. 44, pp. 5279-5285 (1984)); anti-sialyl Lewis a, (D. Chia et al, *Cancer Res.*, vol. 45, pp. 435-437 (1985)); anti-VIM-2 antibody, (B. A. Macher et al, *J. Biol. Chem.*, vol. 263, pp. 10186-10191 (1988)); fluorescein-conjugated goat anti-mouse IgM and IgG antibodies; Sigma). MECA-79 (P. R. Streeter et al, *J. Cell Biol.*, vol. 107, pp. 1853-1862 (1988)) was the generous gift of Drs. Louis Picker and Eugene Butcher (Stanford University).

cDNA cloning. Mouse Fuc-TVII cDNAs were isolated from a cDNA library constructed from the mouse cytotoxic T cell line 14-7fd (P. L. Smith et al, *J. Biol. Chem.*, vol. 269, pp. 15162-15171 (1994)), using colony hybridization procedures (T. Maniatis et al, *Molecular Cloning: A Laboratory Manual*, Cold Spring Harbor Laboratory, Cold Spring Harbor, N.Y. (1982)) and a segment of the mouse Fuc-TVII gene (FIG. 2) corresponding to nucleotides 2053-2285.

Murine genomic library screening. Approximately $1.0 \times 10^6$ recombinant lambda phage from a genomic library prepared from mouse 3T3 cell DNA (Stratagene) were screened by plaque hybridization, using a 324 bp segment of the human Fuc-TIII gene (nucleotides 571-894), and low stringency hybridization procedures described previously (K. M. Gersten et al, *J. Biol. Chem.*, vol. 270, pp. 25047-25056 (1995); K. M. Gersten et al, Doctoral Thesis, pp. 66-98, University of Michigan, Ann Arbor, Mich. (1995)). DNA from a phage with a unique restriction pattern was digested with SacI and a 2.6 kb fragment which cross-hybridized with the human Fuc-TIII probe was gel purified and cloned into the SacI site of pTZ19R (Pharmacia LKB Biotechnology, Inc.). A representative subclone containing a single insert was designated pMFuc-TVII. The DNA sequence of the 2.6 kb insert was determined by the dideoxy chain termination method (F. Sanger et al, *Proc. Natl. Acad. Sci. U.S.A.*, vol. 74, pp. 5463-5467 (1977)) using T7 DNA polymerase (Sequenase, United States Biochemical Corp.) and oligonucleotide primers synthesized according to flanking plasmid sequences. Sequence data was used to design additional synthetic primers which were then utilized to sequence the remaining portion of the SacI insert in pMFuc-TVII. Sequence analysis was performed using the sequence analysis software package of the University of Wisconsin Genetics Computer Group (GCG) (J. Devereux et al, *Nucleic Acids Res.*, vol. 12, pp. 387-395 (1984)) and the MacVector version of the IBI Pustell Sequence Analysis Software package (IBI). Sequence alignments were assembled with the Gap function of the GCG package.

Transfection and analysis of COS-7 cells and CHO-Tag cells. COS-7 cells were transfected with various Fuc-TVII expression vectors using a DEAE-dextran transfection procedure previously described (J. F. Kukowska-Latallo et al, *Genes & Dev.*, vol. 4, pp. 1288-1303 (1990); T. Maniatis et al, *Molecular Cloning: A Laboratory Manual*, Cold Spring Harbor Laboratory, Cold Spring Harbor, N.Y. (1982)). CHO-Tag cells were transfected with plasmid DNAs using a liposome-based reagent (N-[2,3-dioleoyloxy)propyl]-N,N,N-trimethy-lammonium methylsulfate, DOTAP, Boehringer Mannheim), as modified previously (P. L. Smith et al, *J. Biol. Chem.*, vol. 269, pp. 15162-15171 (1994)).

Transiently transfected cells were harvested 72 hours after transfection, and were stained with monoclonal antibodies diluted in staining media, as previously described (B. W. Weston et al, *J. Biol. Chem.*, vol. 267, pp. 24575-24584 (1992)). Anti-Lewis a, anti-H, and anti-sialyl Lewis x antibodies were used at 10 μg/ml. Anti-Lewis x was used at a dilution of 1:1000. Anti-sialyl Lewis a was used at a dilution of 1:500. Anti-VIM-2 antibody was used at a dilution of 1:200. Cells were then stained with fluorescein isothiocyanate-conjugated goat anti-mouse IgM or anti-mouse IgG and subjected to analysis on a FACScan (Becton-Dickinson) as previously described (B. W. Weston et al, *J. Biol. Chem.*, vol. 267, pp. 24575-24584 (1992)). Cells were also co-transfected with the plasmid pCDM8-CAT (P. L. Smith et al, *J. Biol. Chem.*, vol. 269, pp. 15162-15171 (1994)), and extracts prepared from these cells were subjected to chloramphenicol acetyltransferase activity assays (P. L. Smith et al, *J. Biol. Chem.*, vol. 269, pp. 15162-15171 (1994)), to allow for normalization of flow cytometry and Western blot data to transfection efficiency.

Fucosyltransferase assays. COS-7 cells transiently transfected with Fuc-TVII expression vectors were harvested 72 hours after transfection, and extracts were prepared from these cells, exactly as previously described (J. F. Kukowska-Latallo et al, *Genes & Dev.*, vol. 4, pp. 1288-1303 (1990); B.

W. Weston et al, *J. Biol. Chem.*, vol. 267, pp. 4152-4160 (1992)). These extracts were subjected to α(1,3)fucosyltransferase assays (B. W. Weston et al, *J. Biol. Chem.*, vol. 267, pp. 24575-24584 (1992)), assembled in a total volume of 20 µl. Reaction mixtures contained 3 µM GDP-[$^{14}$C]fucose, 20 mM acceptor (N-acetyllactosamine, lactose, lacto-N-biose I, 2'-fucosyllactose (Sigma), or 3' sialyl N-acetyllactosamine (Oxford Glycosystems)), 50 mM cacodylate buffer, pH 6.2, 5 mM ATP, 10 mM L-fucose, 15 mM MnCl$_2$ and a quantity of cell extract protein sufficient to yield approximately linear reaction conditions (consumption of less than 15% of the GDP-fucose substrate) during the course of the reaction (1 h). Control reactions were prepared by omitting the acceptor in the reaction mixture, and values obtained with these reactions were subtracted from the corresponding acceptor-replete reaction. This background radioactivity reproducibly represented less than 1% of the total radioactivity in the assays, and corresponds to free [$^{14}$C]fucose present in the GDP-[$^{14}$C]fucose as obtained from the manufacturer. Identical enzyme preparations were used in assays for the determination of enzyme activity with different acceptor substrates.

Reactions containing neutral acceptors (N-acetyllactosamine, lactose, lacto-N-biose I, 2'-fucosyllactose, all from Sigma) were terminated by the addition of 20 µl ethanol and 560 µl water. Samples were centrifuged at 15,000×g for 5 minutes and a 50 µl aliquot was subjected to scintillation counting to determine the total amount of radioactivity in the reaction. An aliquot of 200 µl was applied to a column containing 400 µl of Dowex 1×2-400, formate form (J. F. Kukowska-Latallo et al, *Genes & Dev.*, vol. 4, pp. 1288-1303 (1990); B. W. Weston et al, *J. Biol. Chem.*, vol. 267, pp. 4152-4160 (1992)). The column was washed with 2 ml of water and the radioactive reaction product, not retained by the column, was quantitated by scintillation counting. Reactions with the acceptor NeuNAcα2→3Galβ1→4GlcNAc (Oxford Glycosystems, Inc.) were terminated by adding 980 µl of 5.0 mM sodium phosphate buffer, pH 6.8. Samples were then centrifuged at 15,000×g for 5 minutes, and a 500 µl aliquot applied onto a Dowex 1×8-200 column (1 ml) prepared in the phosphate form. The reaction product was collected and quantitated as previously described (B. W. Weston et al, *J. Biol. Chem.*, vol. 267, pp. 24575-24584 (1992)).

Generation of rabbit anti-Fuc-TVII antibody. The PCR was used to amplify a segment of the murine Fuc-TVII gene corresponding to the enzyme's "stem" and catalytic domains (J. B. Lowe, *Seminars in Cell Biology*, vol. 2, pp. 289-307 (1991)), using PCR primers corresponding to base pairs 2194-2224 and 3053-3085; FIG. 2; 5' primer gcgc ggatccCACCATCCTTATCTGGCACTGGCCTTTCACC [SEQ ID NO:3]; 3' primer gcgc ggatccAGTTCAAGCCTGGAACCAGCTTTCAAGGTCTTC [SEQ ID NO:4]; BamHI sites underlined). The PCR was completed using twenty rounds of amplification consisting of a 1.5 minute 94° C. denaturation step and a 2.0 minute 72° C. annealing/extension step. The PCR product was subsequently cloned into the BamHI site of the T7 *Escherichia coli* expression vector pET-3b (F. W. Studier et al, *Methods Enzymol.*, vol. 185, pp. 60-89 (1990)). The insert in one clone (termed pET-3b-Fuc-TVIIstem/cat) containing a single insert in the correct orientation was sequenced to confirm that no errors were introduced during DNA amplification. The recombinant Fuc-TVII fusion protein was produced by inducing mid-log phase *E. coli* (BL21 Lys S) carrying pET-3b-Fuc-TVIIstem/cat with 0.4 mM IPTG for three hours (K. M. Gersten et al, Doctoral Thesis, pp. 66-98, University of Michigan, Ann Arbor, Mich. (1995); F. W. Studier et al, *Methods Enzymol.*, vol. 185, pp. 60-89 (1990)). The bacteria were subsequently harvested, and lysed by freezing and then thawing the bacterial suspension. Bacterial genomic DNA was sheared by sonication, followed by separation of soluble and insoluble material by centrifugation. The Fuc-TVII protein was found in the insoluble fraction, as determined by SDS-polyacrylamide electrophoresis (E. Harlow et al, *Antibodies: A Laboratory Manual*, Cold Spring Harbor Laboratory, Cold Spring Harbor, N.Y. (1988)).

Recombinant, *E. coli*-derived Fuc-TVII was fractionated by SDS-polyacrylamide gel electrophoresis, and segments of the gel containing Fuc-TVII were excised and used subsequently as antigen for rabbit immunizations. Rabbit immunization services were purchased (Pel-Freeze Biologicals; Rogers, Ariz.). Each of three rabbits were initially immunized subcutaneously with a total of approximately 200 µg of Fuc-TVII in pulverized polyacrylamide gel slices, mixed with complete Freund's adjuvant. Subsequent immunizations were completed in an essentially identical manner, at 14 day intervals, except that antigen was administered in incomplete Freund's adjuvant. Antisera were harvested ten days following the last of a total of approximately 6 secondary immunizations.

Antigen affinity purification of anti-Fuc-TVII antibody. The insert in pET-3b-Fuc-TVIIstem/cat was released by digestion with BamHI and was cloned between the BamHI sites in the *E. coli* expression vector pATH10 (T. J. Koerner et al, *Methods Enzymol.*, vol. 194, pp. 477-490 (1991)), to yield a fusion protein derived from the *E. coli* anthranilate synthase sequence, fused in frame to Fuc-TVII sequence. This recombinant fusion protein was expressed in *E. coli* strain DH5α (induction for 6 hr with 0.0125% indoleacrylic acid in M9 medium). The bacteria were harvested, washed, and disrupted by treating with lysozyme (3 mg/ml) in 50 mM Tris HCl pH 7.5, 5 mM EDTA, with 0.65% NP-40, 0.38M NaCl, followed by sonication for 20 sec at the maximal microtip setting (Vibracell, Sonics and Materials, Inc., Danbury, Conn.) (T. J. Koerner et al, *Methods Enzymol.*, vol. 194, pp. 477-490 (1991)). Inclusion bodies were washed twice with 50 mM Tris HCl pH 7.5, 5 mM EDTA, were solubilized by heating to 100° C. in 1% SDS, 12 mM Tris HCl, 5% glycerol, 1% 2-mercaptoethanol, and were subjected to SDS-polyacrylamide gel electrophoresis. The fractionated proteins were transferred to PVDF membrane (Bio-Rad Laboratories, Hercules, Calif.) by electroblotting (1 mA/cm$^2$). The membrane was then blocked for 4-6 hr at 4° C. with PBS containing 10% bovine serum albumin, and 0.2% Tween-20. A strip of membrane containing the recombinant Fuc-TVII fusion protein was incubated overnight at 4° C. with 0.5 ml rabbit anti-mouse Fuc-TVII antiserum, diluted with 2.5 ml of PBS containing 3% bovine serum albumin and 0.2% Tween-20. The membrane was then washed at room temperature in PBS, 0.05% Tween-20, sliced into small pieces, and the bound antibody was eluted by incubating the membrane fragments on ice for 10 min in 450 µl Tris-Glycine pH 2.5. The supernatant was collected and immediately neutralized with 100 µl of 1M Tris-HCl pH 8.0. The elution procedure was completed a second time, and the two eluates were pooled and used subsequently for immunohistochemical procedures.

Western blot analysis. Cell extracts were prepared from transfected COS-7 cells 72 h after transfection. Extracts contained 50 mM Tris-HCl (pH 6.8), 1% SDS, and 10% glycerol. Extracts were boiled for 3 min immediately after preparation, and were stored frozen until use. Protein content was determined using the BCA reagent procedure. Extracts were prepared for SDS-PAGE by adding dithiothreitol to a final concentration of 0.1 M, and bromophenol blue to a final concentration of 0.05%. Samples were then boiled, and fractionated by electrophoresis through a 10% SDS-polyacrylamide gel. After electrophoresis, the proteins were electrotransferred to a PVDF membrane (Biorad). The membrane was rinsed, and then blocked for 12-14 h at 4° C. in phosphate buffered saline, pH 7.4, containing 10% bovine serum albumin and 0.2% Tween-20. The blot was washed at room temperature in phosphate buffered saline, pH 7.4, 0.2% Tween-20, and was probed with a 1:200 dilution of antigen affinity purified rabbit anti-Fuc-TVII antibody. The blot was then washed and probed with a 1:2500 dilution of a horse radish peroxidase-conjugated anti-rabbit immunoglobulin (Sigma). The blot was then rinsed, exposed to ECL reagent (Amersham, UK), and subjected to autoradiography.

Northern blot analysis. Total RNA was prepared from mouse (FVB/N) tissues and cultured cell lines, using published procedures (T. Maniatis et al, *Molecular Cloning: A Laboratory Manual*, Cold Spring Harbor Laboratory, Cold Spring Harbor, N.Y. (1982)). Oligo-dT-purified polyA+ RNA samples were electrophoresed through 1.0% agarose gels containing formaldehyde, and were transferred to a nylon membrane (Hybond-N, Amersham). Northern blots were prehybridized for 2 hours at 42° C. in 1×PE, 5×SSC, 0.5% sodium dodecyl sulfate, and 150 µg/ml sheared salmon sperm DNA. Blots were hybridized for 18 hours at 42° C. in prehybridization solution containing $\alpha[^{32}P]$-labeled 974 bp EagI-EcoRI fragment isolated from the insert in pMFuc-TVII. The EagI site is located at nucleotides 2228-2233 while the EcoRI site spans base pairs 3202-3207. Blots were stripped in boiling 0.1% SDS and re-hybridized with a chicken glyceraldehyde 3-phosphate dehydrogenase probe (A. Dugaiczyk et al, *Biochemistry*, vol. 22, pp. 1605-1613 (1983)) to confirm that RNA samples were intact and loaded in equivalent amounts.

Construction of a mouse L-Selectin/IgM chimera histochemical probe. A mouse L-selectin cDNA (M. H. Siegelman et al, *Science*, vol. 243, pp. 1165-1172 (1989)) was kindly provided by Dr. Mark Siegelman at the University of Texas Southwestern Medical Center, Dallas, Tex. The extracellular domain was truncated at the junction of its transmembrane domain with an Hph I digest followed by the litigation of an adaptor. A human IgM cDNA containing the CH2, CH3, and CH4 domains (kindly provided by Dr. Ernie Kawasaki, Procept Inc.) was ligated to the adaptor modified end of the L-selectin sequence in a manner that fuses the open reading frame encoding L-selectin to the open reading frame encoding the CH2, CH3, and CH4 domains of human IgM. This fragment was inserted into the vector SRα-PCDM8 immediately downstream of the SRα promoter in the sense orientation with respect to the SRα promoter. This vector was introduced into COS-7 cells using the DEAE dextran transfection method (J. F. Kukowska-Latallo et al, *Genes & Dev.*, vol. 4, pp. 1288-1303 (1990); T. Maniatis et al, *Molecular Cloning: A Laboratory Manual*, Cold Spring Harbor Laboratory, Cold Spring Harbor, N.Y. (1982)). Media was harvested from the transfected cells 3 days after the transfection, and was replaced with fresh media (DMEM, 10% FCS, P/S, Q) that was collected 4 days later. The L-selectin/IgM chimera was purified and concentrated approximately 40-fold by affinity chromatography on goat anti-human IgM agarose.

Immunohistochemistry procedures. Peripheral (axillary) and mesenteric lymph nodes, and Peyer's patches were isolated from mice immediately after sacrifice. These lymphoid tissues were embedded in OCT medium (Tissue-Tek, MILES, Elkhart, Ind.), sectioned with a Leica 2800N cryostat, and collected on glass microscope slides.

Sections to be stained with anti-Fuc-TVII were fixed in 2% paraformaidehyde in phosphate buffered saline for 20 min on ice. The sections were rinsed with phosphate buffered saline at room temperature, were quenched with 50 mM $NH_4Cl$ in phosphate buffered saline at room temperature, and then rinsed briefly with water. The tissues were then permeabilized with 100% methanol for 20 min on ice, rehydrated in phosphate buffered saline, and then incubated for 30 min at room temperature with blocking solution A (phosphate buffered saline containing 2% goat serum, 0.05% Triton X-100, 0.05% Tween 20). The blocking solution was aspirated, and the sections were incubated overnight at 7° C. with antigen affinity purified anti-Fuc-TVII, used at a final concentration of 5 µg/ml, in blocking solution A. After the overnight incubation, the anti-Fuc-TVII/blocking solution was removed, the slides were washed with phosphate buffered saline, and were incubated for 1 hr at room temperature with a FITC-conjugated goat anti-rabbit IgG reagent (Sigma), diluted 1:200 in blocking solution A. The slides were then washed at room temperature in phosphate buffered saline, mounted with citifluor (Citifluor Products, Chemical Laboratory, The University, Canterbury, Kent CT2 7NH), and examined by immunofluorescence microscopy (Leitz DM RB microscope).

Sections to be stained with the monoclonal antibody MECA-79 (P. R. Streeter et al, *J. Cell Biol.*, vol. 107, pp. 1853-1862 (1988)) were fixed on ice for 20 min in 2% paraformaldehyde in phosphate buffered saline, washed at room temperature with phosphate buffered saline, and were quenched for 20 min at room temperature with 50 mM $NH_4Cl$ in phosphate buffered saline. The slides were then rinsed briefly in water, permeabilized with 100% methanol for 20 min on ice, rehydrated in phosphate buffered saline, and then incubated overnight at room temperature with blocking solution A (phosphate buffered saline containing 2% goat serum, 0.05% Triton X-100, 0.05% Tween 20). The blocking solution was then aspirated, and the sections were incubated for 1 hr at 7° C. with MECA-79 at a concentration of 5 µg/ml in blocking solution A. Sections were then washed extensively with phosphate buffered saline at room temperature. The washed sections were then incubated for 1 hr at room temperature with a TRITC-conjugated goat anti-rat IgM reagent (Jackson ImmunoResearch, Pennsylvania), used at a dilution 1:200 in blocking solution A. The slides were then washed 3 times at room temperature with phosphate buffered saline, mounted with citifluor, and examined.

Sections to be stained with the L-selectin/IgM chimera were fixed in 1% paraformaldehyde, 0.1M cacodylate, pH 7.1, for 20 min on ice, and were then washed with Tris-buffered saline, pH 7.4. The L-selectin/IgM chimera was applied to the sections at a concentration 60 µg/ml, in blocking solution B (Tris-buffered saline, pH 7.4, containing 2% goat serum), supplemented with either 3 mM $CaCl_2$, or with 5 mM EDTA, and were allowed to incubate overnight at 7° C. Sections were then washed extensively with ice cold Tris-buffered saline supplemented with 3 mM $CaCl_2$. Sections were then incubated for 1 hr at 7° C. with a biotinylated goat anti-human IgM reagent (Sigma), diluted 1:200 in blocking solution B, and supplemented either with 3 mM $CaCl_2$, or with 5 mM EDTA. The sections were then washed with ice cold Tris-buffered saline supplemented with 3 mM $CaCl_2$, and were incubated for 1 hr at 7° C. with a FITC-conjugated streptavidin reagent (Vector Labs, Burlingame, Calif.) diluted 1:200 in blocking solution B supplemented with 3 mM $CaCl_2$. The slides were washed with ice cold Tris-buffered saline supplemented with 3 mM $CaCl_2$, mounted with citifluor, and examined by immunofluorescence microscopy (Leitz DM RB microscope).

In situ hybridization procedures. In situ hybridization procedures were completed using a modification of published procedures (D. G. Wilkinson *In Situ Hybridization: A Practical Approach, IRL Press, Oxford University Press, Oxford, UK). Fresh murine axillary lymph nodes, mesenteric lymph nodes and Peyer's patches were embedded in OCT medium (Tissue-Tek, MILES, Elkhart, Ind.) and quick-frozen in isopentane on liquid nitrogen. Cryostat sections (10 µM) were collected on Superfrost/Plus microscope slides (Fisher Scientific, Pittsburgh, Pa.), fixed in freshly prepared 4% paraformaldehyde in PBS for 30 min on ice, washed twice in PBS and digested for 5 min at room temperature with 1 µg/ml proteinase K in 50 mM Tris HCl pH 7.5, 5 mM EDTA. The slides were then washed in PBS, fixed again in 4% paraformaldehyde, rinsed in water, and treated with 0.25% acetic anhydride in 0.1M triethanolamine pH 8.0, for 10 min at room temperature. Acetylation was followed by room temperature washes in PBS, and then in 0.85% NaCl. The slides were then dehydrated in a graded series of solutions of ethanol in water (30%, 50%, 80%, 95%, 100% ethanol). Air dried sections were overlaid with a hybridization solution containing $^{35}$S-labeled RNA, in sense or antisense orientation. RNA probes were derived by in vitro transcription procedures, using recombinant T7 or Sp6 RNA polymerases, initiating on the T7 or Sp6 promoter sequences flanking a DNA segment derived from the coding region of the mouse Fuc-TVII gene (base pairs 2197-2494; FIG. 2), as subcloned into the vector pcDNAI (Invitrogen). The hybridization solution contained 50% deionized formamide, 0.3 M NaCl, 20 mM Tris HCl pH 8.0, 5 mM EDTA, 10 mM phosphate buffer pH 8.0, 10% dextran sulphate, 1×Denhardt's solution (T. Maniatis et al, *Molecular Cloning: A Laboratory Manual*, Cold Spring Harbor Laboratory, Cold Spring Harbor, N.Y. (1982)), 0.5 mg/ml yeast tRNA, 10 mM dithiothreitol, and $10^7$ cpm/ml of radiolabeled probe. The hybridization solution was sealed over the sections with a coverslip and DPX mounting media (BDH Lab Supplies, Poole, England). Hybridization was carried out for 16 hours at 55° C. in a sealed container humidified with 5× Standard Saline Citrate (SSC). After hybridization, the DPX mounting media seal was removed, and slides were washed at 55° C. for 30 min in 5×SSC, 10 mM dithiothreitol, and then at 65° C. for 30 min in formamide wash buffer (50% formamide, 2×SSC, 20 mM dithiothreitol). The slides were then washed 4 times at 37° C. in 0.5 M NaCl, 10 mM Tris HCl pH 7.5, 5 mM EDTA. Slides were then digested with RNAseA (1 µg/ml) for 30 min at 37° C., and were washed in formamide buffer, then in 2×SSC, and then in 0.1×SSC. Slides were dehydrated in a graded series of solutions of ethanol in 0.3 M ammonium acetate (30%, 50%, 80%, 95%, 100% ethanol), air dried, and were coated with NTB2 liquid emulsion (Kodak). Following a two to three week exposure time, the emulsion was developed using procedures suggested by the manufacturer. Sections were then stained with hematoxylin and eosin, and examined and photographed with bright field and dark field modalities, using a Leitz DM RB microscope.

Results

A hybridization screen identifies a novel murine α(1,3) fucosyltransferase locus. In an effort to isolate novel murine α(1,3)fucosyltransferase genes, a murine genomic DNA phage library was screened with a probe corresponding to the catalytic domain of the human Lewis α(1,3/1,4)fucosyltransferase (Fuc-TIII) (J. F. Kukowska-Latallo et al, *Genes & Dev.*, vol. 4, pp. 1288-1303 (1990)), using low stringency hybridization conditions (see the Experimental Procedures). One phage was isolated that contained an insert with a translational reading frame sharing approximately 40% amino acid sequence similarity with the amino acid sequences encoded by four previously cloned members of the human α(1,3) fucosyltransferase family (Fuc-TIII-VI) (J. F. Kukowska-Latallo et al, *Genes & Dev.*, vol. 4, pp. 1288-1303 (1990); B. W. Weston et al, *J. Biol. Chem.*, vol. 267, pp. 24575-24584 (1992); B. W. Weston et al, *J. Biol. Chem.*, vol. 267, pp. 4152-4160 (1992); J. B. Lowe et al, *J. Biol. Chem.*, vol. 266, pp. 17467-17477 (1991); S. E. Goelz et al, *Cell*, vol. 63, pp. 1349-1356 (1990); R. Kumar et al, *J. Biol. Chem.*, vol. 266, pp. 21777-21783 (1991)).

To identify transcripts corresponding to this genomic sequence, a segment of the phage insert representative of the open reading frame was used to probe Northern blots prepared from mouse cell lines and tissues. Transcripts corresponding to this probe were identified in the murine cytotoxic T-cell line 14-7fd (T. J. Braciale et al, *J. Ex. Med.*, vol. 153, pp. 910-923 (1981); M. E. Andrew et al, *J. Immunol.*, vol. 132, pp. 839-844 (1984)). A cDNA library constructed from this cell line (P. L. Smith et al, *J. Biol. Chem.*, vol. 269, pp. 15162-15171 (1994)) was screened by hybridization with a segment of the phage insert, yielding 16 hybridization positive colonies. The sequences of all 16 cDNA clones were determined, as was the sequence of the corresponding genomic DNA (FIG. 1a). Analysis of this sequence data indicates that this locus yields multiple, structurally-distinct transcripts derived from alternative splicing events, and possibly also from alternative transcription initiation events. Five classes of cDNAs were identified (FIG. 1). Analysis of these cDNA sequences identifies three methionine codons that may function to initiate translation of an open reading frame with amino acid sequence similarity to human Fuc-TIII, Fuc-TIV, Fuc-TV, and Fuc-TVI (FIG. 2). The positions of these methionine codons predicts the synthesis of α(1,3)fucosyltransferases with different cytosolic domains (encoded by exons 2 and/or 3), but with identical Golgi-localized catalytic domains (encoded by exon 4). One relatively abundant class of cDNAs (represented by cDNA 14) maintains an open reading frame initiating at the methionine codon at nucleotide 1947. This reading frame predicts a 342 residue, 39,424 Da type II transmembrane protein, with a hydrophobic, transmembrane segment derived from amino acids 9-31 (FIG. 2). An in-frame methionine codon at nucleotide 2126 predicts a 318 residue, 36,836 Da polypeptide that initiates within the hydrophobic, transmembrane segment of the polypeptide predicted by the longer reading frame initiated at nucleotide 1947. A similar structural arrangement is found in two other cDNA classes, represented by cDNAs 6 and 10. However, these two cDNAs differ from cDNA 14 in that they contain an additional upstream exon with a methionine codon corresponding to nucleotide 996. The translational reading frame initiated by this methionine codon is truncated by a termination codon in exon 2 at a position proximal to the methionine codon at nucleotide 1947, and thus cannot generate a polypeptide that shares similarity to the human α(1,3)fucosyltransferases. However, in cDNA 5, absence of exon 2 allows the translational reading frame generated by the methionine codon at nucleotide 996 to continue in frame with sequence in exon 4. This arrangement predicts the synthesis of a 389 residue, 44,492 Da type II transmembrane protein, with the same putative transmembrane segment defined for the protein predicted by cDNA 14 (FIG. 2). Finally, cDNA 3 is representative of a relatively abundant class of cDNAs that each initiate between the splice acceptor site of exon 4 and the methionine codon at nucleotide 2126. This class of cDNAs predicts a 318 residue, 36,836 Da polypeptide that initiates within the transmembrane segment predicted for the proteins corresponding to the other cDNA classes.

Because the polypeptides predicted by these murine cDNAs share primary sequence similarity to the four human α(1,3)fucosyltransferases known at the time (Fuc-TIII, IV, V, and VI), we anticipated that one or more of them would function as an α(1,3)-fucosyltransferase. However, because the murine peptide sequence shares approximately equivalent sequence similarity to each of these human enzymes, we expected that it did not represent the murine homologue of any of them, and consequently named it Fuc-TVII. This appellation has been justified by subsequent work in which this murine gene has been used to isolate cDNAs encoding the human Fuc-TVII (S. Natsuka et al, *J. Biol. Chem.*, vol. 269, pp. 16789-16794 (1994)).

None of the three putative initiation codons are embedded in a sequence context consistent with Kozak's rules for translation initiation (FIG. 2) (M. Kozak, *Cell*, vol. 44, pp. 283-292 (1986)). To determine which, if any, of these initiation codons and cognate cDNAs function to encode the predicted polypeptide(s), and to confirm that this locus encodes an α(1,3)fucosyltransferase, COS-7 cells were transfected with a cDNA representative of each class, and the transfectants were subjected to assays to (i) identify cDNA-determined cell surface-localized fucosylated oligosaccharide antigens, (ii) identify and quantitate the polypeptides encoded by cDNAs, and (iii) identify and partially characterize cDNA-determined α(1,3)fucosyltransferase activity in transfectant cell extracts using in vitro α(1,3)fucosyltransferase activity assays.

cDNAs representative of three of the five classes (cDNAs 6, 10, and 14) (FIG. 1) each determine relatively high levels of cell surface-localized sLe$^x$ expression (35.1%, 21.8%, and 16.5%, respectively, above a 2% background) when introduced into COS-7 cells by transfection. cDNA 5 also directs cell surface sLe$^x$ expression in COS-7 cells, but at a level (9% positive cells) that is lower than the sLe$^x$ expression levels determined by cDNAs 6, 10, and 14. By contrast, none of these four cDNAs directs expression of Lewis x, Lewis a, or sialyl Lewis a determinants. These results indicate that on or both of the two potential methionine initiator codons in each cDNA can efficiently direct translation to yield α(1,3)fucosyltransferase activity. These observations further indicate that this α(1,3)fucosyltransferase activity can utilize α(2,3) sialylated lactosamine-based glycan structures to form sLe$^x$ determinants, but indicate that the activity does not efficiently utilize neutral type II oligosaccharide Lewis x precursors, nor neutral or α(2,3)sialylated type I precursors to the Lewis a isomers. Since all four of these cDNAs direct qualitatively identical cell surface antigen profiles in COS-7 cells, it seems likely that individually, or together, each directs the expression of polypeptides that individually, or together, maintain essentially identical acceptor substrate specificities (at least for the four antigens examined).

In contrast to the results obtained with cDNAs 5, 6, 10, and 14, cDNA 3 does not direct detectable sLe$^x$ expression. This result suggests that the methionine codon at nucleotide 2126 in this cDNA does not efficiently promote initiation of translation of the cognate mRNA, and thus does not encode functionally significant levels of enzyme activity. Alternatively, this cDNA may encode a polypeptide without α(1,3)fucosyltransferase activity.

Qualitatively identical results were obtained when these five cDNAs were expressed in another cell line (CHO-Tag cells) (P. L. Smith et al, *J. Biol. Chem.*, vol. 269, pp. 15162-15171 (1994)) informative for expression of the Lewis x, and sLe$^x$ determinants. Unlike COS-7 cells, this cell line is also capable of forming the internally fucosylated VIM-2 determinant (NeuAcα2,3Galβ1,4GlcNAcβ1,3Galβ1,4(Fucα1,3) GlcNAc-R) (B. W. Weston et al, *J. Biol. Chem.*, vol. 267, pp. 24575-24584 (1992)). It was found that none of the cDNAs directs expression of the VIM-2 epitope when expressed in the CHO-Tag cells. Considered together, these results indicate that some, though not all, of the cDNAs can encode an α(1,3)fucosyltransferase activity that can catalyze α(1,3)fucosylation of the N-acetylgalactosamine moiety on a terminal α(2,3)sialylated lactosamine unit, but not to internal N-acetylgalactosamine moieties on α(2,3)sialylated polylactosamine precursors, nor to neutral type II precursors.

Figure 1B:
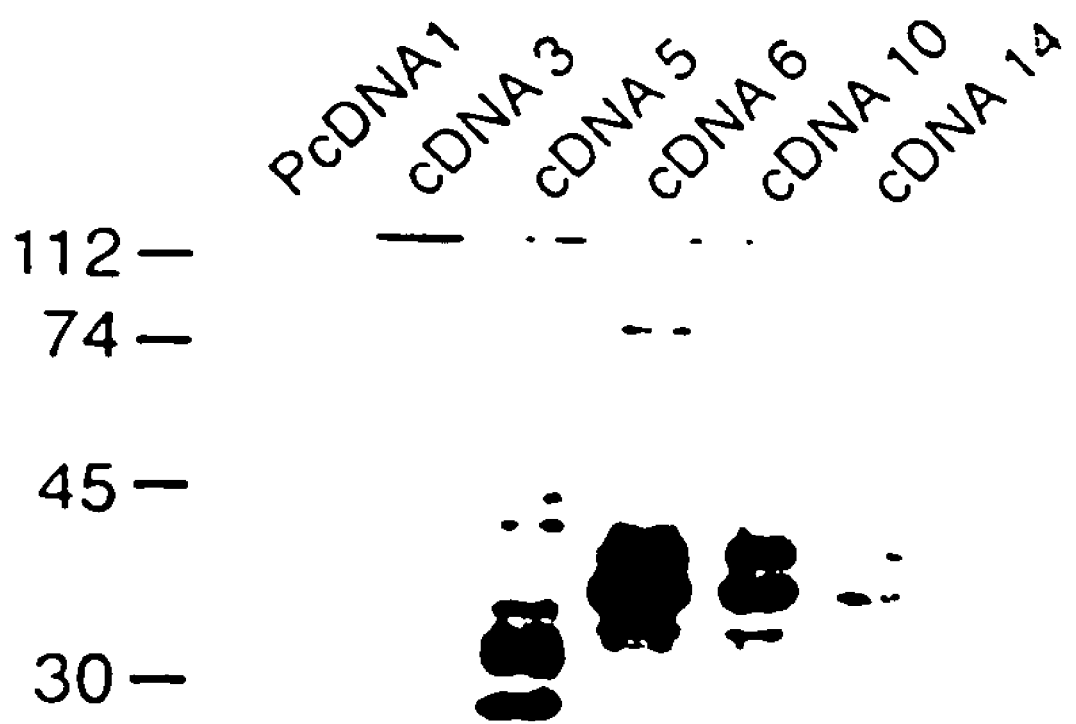
FIG. 1b shows the results of a Western blot analysis of the polypeptides expressed in COS-7 cells by cDNAs 3, 5, 6, 10, and 14. The extracts used in the α(1,3)fucosyltransferase assays shown in FIG. 1a, above, were also subjected to Western blot analysis using an antigen-affinity purified anti-Fuc-TVII antibody. The amounts of protein analyzed from each type of transfected cell extract were varied to achieve normalization to the transfection efficiencies, exactly as indicated above in FIG. 1a for the flow cytometry and α(1,3)fucosyltransferase activity analyses. Cell extracts were fractionated by SDS-polyacrylamide gel electrophoresis, electro-blotted to a PVDF membrane, and the Fuc-TVII expression vector-encoded polypeptides were identified by probing with an antigen affinity purified rabbit anti-Fuc-TVII antibody, goat anti-rabbit IgG-peroxidase conjugate, and a commercially available enhanced chemiluminescence reagent (ECL, Amersham), as described in the Experimental Procedures in the Examples.

To confirm that the sLex expression efficiency characteristic of each cDNA correlates with the level of expression of the corresponding protein, cell extracts of the transfected COS-7 cells were subjected to Western blot analysis using an affinity purified rabbit polyclonal antibody generated against a recombinant form of the predicted polypeptide (FIG. 1b). Cells transfected with cDNAs 6, 10, and 14 express two major forms of the protein, with molecular weights of 35 kDa and 37 kDa. Smaller amounts of several other proteins are also evident in these cells. The amount of immunoreactive protein generated by these three cDNAs correlates with the level of sLex expression directed by each. This observation indicates that the relative sLex expression level directed by each is a function of the efficiency with which each corresponding mRNA is translated, and thus the relative intracellular accumulation of the cognate polypeptide.

Cells transfected with cDNA 5 also contain multiple immunoreactive polypeptides (FIG. 1b). The most abundant pair of these proteins migrate more rapidly than do the proteins detected in cells transfected with cDNAs 6, 10, and 14, yet are approximately similar in quantity to the immunoreactive protein directed by cDNAs 6 and 10. As cDNA 5 directs lower levels of cell surface sLex expression than these two cDNAs, it is therefore possible that the lower Mr immunoreactive polypeptides found in cDNA 5-transfected cells-maintain substantially lower specific enzyme activity than do the proteins encoded by cDNAs 6, 10, and 14, or are otherwise less able to direct sLex expression in COS-7 cells. Finally, cells transfected with cDNA 3 do not contain any detectable immunoreactive proteins. This implies that the putative initiator codon at base pair 2126 in this cDNA does not initiate translation of an immunoreactive product, and is consistent with the observation that this cDNA does not yield sLex expression following transfection into COS-7 cells.

Conclusions derived from the flow cytometry and Western blot analyses summarized above are supported by the results of in vitro α(1,3)fucosyltransferase assays completed on the same cell extracts. These assays demonstrate that cells transfected with cDNAs 5, 6, 10, and 14 contain enzyme activity that can transfer $^{14}$C-labelled fucose from the nucleotide donor substrate GDP-fucose to the low molecular weight acceptor 3'-sialyl-N-acetyllactosamine (SLN; NeuNAcα2, 3Galβ1,4GlcNAc) (FIG. 1a). For each cDNA, the product of this reaction co-elutes with a radiolabeled sLe$^x$ tetrasaccharide standard when fractionated by ion suppression amine adsorption HPLC. The α(1,3)fucosyltransferase activity directed by each of these four cDNAs does not utilize the neutral acceptor substrates N-acetyllactosamine or lacto-N-biose I. And, extracts prepared from cells transfected with cDNA 3 do not contain detectable α(1,3)fucosyltransferase activity when tested with 3'-sialyl-N-acetyllactosamine, nor when tested with the neutral acceptor substrates N-acetyllactosamine or lacto-N-biose I. These results are entirely consistent with the flow cytometry data summarized above, and indicate that this locus encodes an α(1,3)fucosyltransferase activity that apparently requires type II acceptor substrates that are terminally substituted with an α(2,3)-linked sialic acid residue. Considered together, these results suggest that differential splicing and/or transcriptional initiation events can control the level of α(1,3)fucosyltransferase activity, and thus cell surface sLex expression level, through mechanisms that depend on the efficiency with which each transcript is translated.

Figures 3A, 3B:
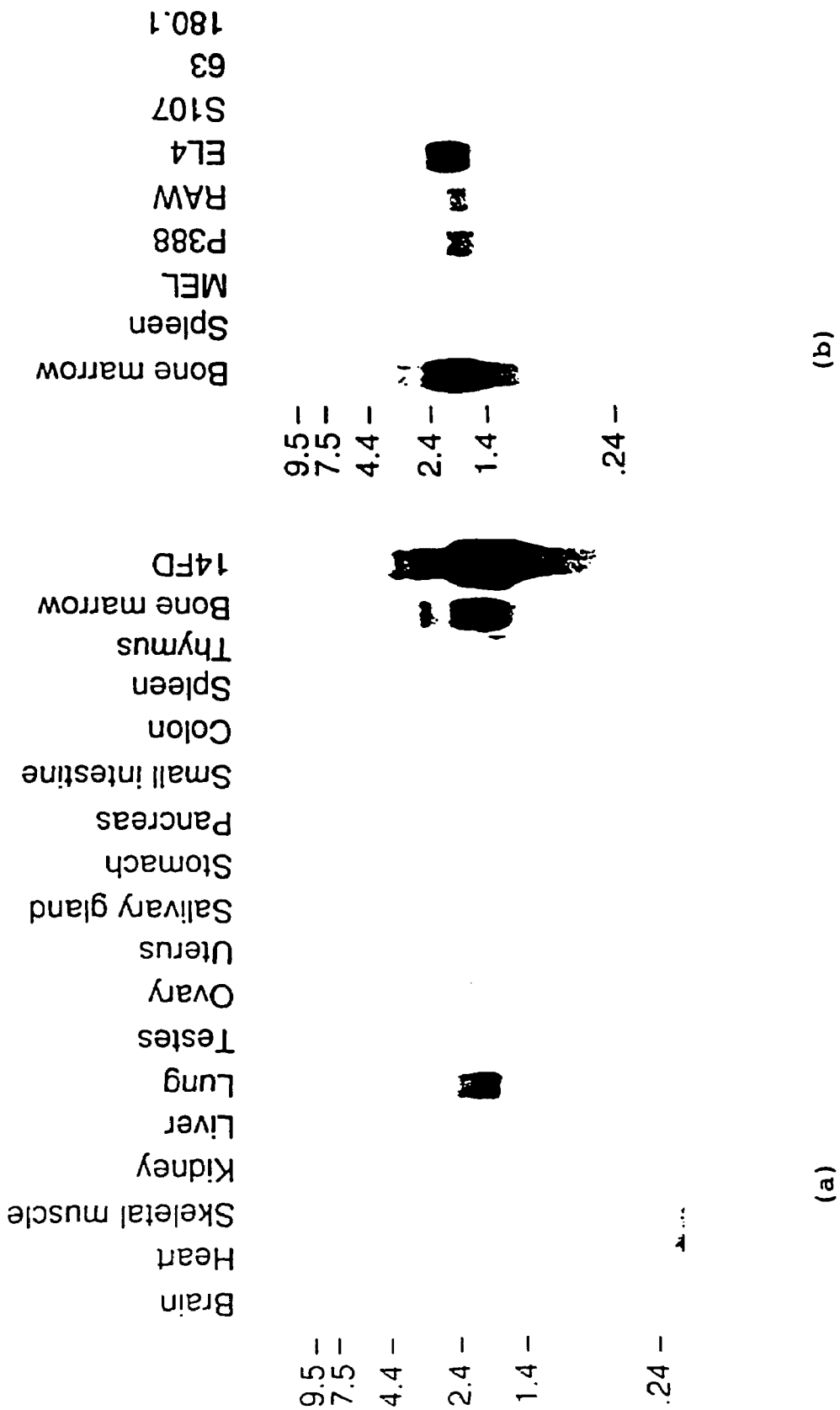
FIGS. 3a and b show the tissue specific expression patterns of the murine Fuc-TVII gene. Oligo-dT purified mRNA (5 µg) purified from murine tissues and cell lines was fractionated by agarose gel electrophoresis, blotted to a nylon hybridization membrane, and was probed with a 979 base pair DNA segment derived from the coding region of the mouse Fuc-TVII locus (nucleotides 2228-3207; see FIG. 2 and the Experimental Procedures in the Examples). RNA molecular size standards, in kb, are indicated at the left in each panel. Each blot was subsequently stripped and re-probed with a radiolabeled chicken glyceraldehyde 3-phosphate dehydrogenase probe to confirm that RNA samples were intact and loaded in equivalent amounts (see the Experimental Procedures in the Examples)
FIG. 3b shows the polyadenylated RNA isolated from mouse bone marrow and spleen, and from cultured murine leukocyte cell lines. Cell lines represent the following lineages: MEL, murine erythroleukemia cell line; P388 and RAW (RAW 264.7), macrophage; EL4, T cell; S107, 63 (TH2.54.63) and 180.1, B cell lines (hybridomas)

Transcription of the mouse Fuc-TVII locus is restricted to cells found in the bone marrow and the lung. Northern blot analysis indicates that transcripts corresponding to the Fuc-TVII locus accumulate to detectable levels in only a few tissues in the adult mouse (FIG. 3). Abundant transcript accumulation is only observed in the lung and in the bone marrow, with very small amounts evident in the spleen, salivary gland, and skeletal muscle. Northern blot analysis of cultured murine blood cell-type cell lines indicates that the Fuc-TVII transcript is relatively abundant in the mouse cytotoxic T line 14-fd (used to clone the Fuc-TVII cDNAs), and in the mouse T cell line EL4 (L. J. Old et al, *Cancer Res.*, vol. 25, pp. 813-819 (1965)). Less abundant transcript accumulation is evident in the murine macrophage-derived lines RAW (P. Ralph et al, *J. Immunol.*, vol. 119, pp. 950-954 (1977); W. C. Raschke et al, *Cell*, vol. 15, pp. 261-267 (1978)) and P388 (H. S. Koren et al, *J. Immunol.*, vol. 114, pp. 894-897 (1975)). Fuc-TVII transcripts are not evident in the murine erythroleukemia cell line MEL (D. Singer et al, *Proc. Natl. Acad. Sci. U.S.A.*, vol. 71, pp. 2668-2670 (1974); B. L. Weber et al, *Science*, vol. 249, pp. 1291-1293 (1990)), nor in three murine B-lymphocyte lineage cell lines [S107, (M. L. Atchison et al, *Cell*, vol. 48, pp. 121-128 (1987)); TH2.54.63, (T. Hamano et al, *J. Immunol.*, vol. 130, pp. 2027-2032 (1983)); 180.1, (M. Hummel et al, *J. Immunol.*, vol. 138, pp. 3539-3548 (1987))].

Both the marrow and lung maintain several differently-sized transcripts, including two abundant transcripts of approximately 1.6 and 2.2 kb in size, and a fainter transcript at approximately 3.0 kb. These three transcripts are similar in size to the three most abundant transcripts observed in the murine 14-7fd cytotoxic T cell line. These observations suggest that cells in the bone marrow and lung yield alternatively spliced transcripts similar in structure to those characterized by cDNA cloning studies in the 14-7fd cells. These data also suggest that in the marrow, the Fuc-TVII locus is transcribed in cells assigned to the myeloid and T-lymphoid lineages, but not in B-lymphoid lineage cell types, and suggest that expression of this fucosyltransferase correlates with selectin ligand expression on myeloid and T-lymphocyte lineage cell types.

Figure 4:
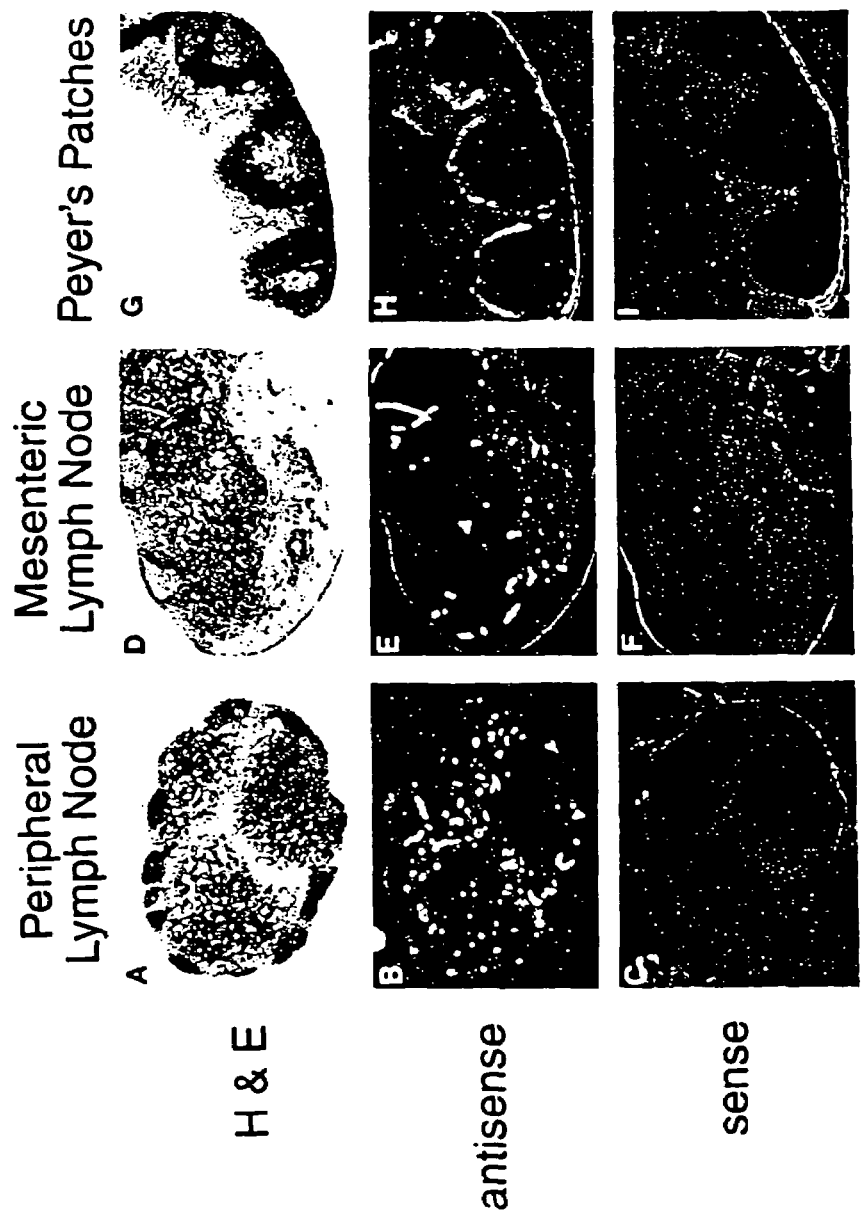
FIG. 4 shows the results of an in situ hybridization analysis of Fuc-TVII transcripts in murine lymph nodes and Peyer's Patches. Sequential 10 micron thick frozen sections of an axillary lymph node (column labeled Peripheral Lymph Node; panels A, B, C), a mesenteric lymph node (column labeled Mesenteric Lymph Node, panels D, E, F), and Peyer's patches (column labeled Peyer's Patches; panels G, H, I), were stained with hematoxylin and eosin (row labeled H & E; panels A, D, G, photograph at 5× magnification using bright field illumination), or were processed for in situ hybridization, as described in the Experimental Procedures in the Examples. Adjacent sections subjected to in situ hybridization were probed with an $^{35}$S-labeled anti-sense RNA probe derived from base pairs 2196-2497 of the murine Fuc-TVII locus (row labeled antisense; panels B, E, H), or were probed with an $^{35}$S-labeled negative control sense RNA probe derived from base pairs 2196-2497 of the murine Fuc-TVII locus (row labeled sense; panels C, F, I). Sections processed for in situ hybridization were photographed at 5× magnification using dark field illumination. The white areas in panels B, E, and H correspond to sites (i.e. high endothelial venular endothelial cells in panels B and E; high endothelial venular endothelial cells and lumenally-positioned cells [the white-stained "caps" on the lymphoid aggregates] in panel H) where the Fuc-TVII antisense probe identifies Fuc-TVII transcripts (see text for details)

Fuc-TVII is expressed in endothelial cells lining the high endothelial venules in peripheral lymph nodes, mesenteric lymph nodes, and Peyer's patches. The identity of the cell types in the lung responsible for the Northern blot signal in that organ was disclosed by in situ hybridization analyses. These studies identified Fuc-TVII transcripts in paratracheal lymph nodes within the extirpated lung, but not in any other cell type. The pattern of expression in these nodes suggested that the Fuc-TVII transcripts were localized to the high endothelial venules within these nodes. When considered together with recent observations suggesting that a sulfated derivative of the sialyl Lewis x determinant represents a terminal oligosaccharide moiety found on HEV-specific L-selectin ligands (S. Hemmerich et al, *Biochemistry*, vol. 33, pp. 4820-4829 (1994); S. Hemmerich et al, *Biochemistry*, vol. 33, pp. 4830-4835 (1994); S. Hemmerich et al, *J. Biol. Chem.*, vol. 270, pp. 12035-12047 (1995)), detection of Fuc-TVII transcripts in these HEV suggests a possible role for this locus in the synthesis of this fucosylated oligosaccharide, and this in controlling lymphocyte homing. To further characterize the HEV-specific expression of Fuc-TVII, this was systematically evaluated using in situ hybridization analysis of HEV in peripheral lymph nodes, in mesenteric lymph nodes, and in Peyer's patches, where L-selectin ligand expression has been well-characterized (S. D. Rosen et al, *Curr. Opin. Cell Biol.*, vol. 6, pp. 663-673 (1994)). These analyses (FIG. 4) indicate that Fuc-TVII transcripts accumulate to easily detectable levels in the HEV of all three types of lymphoid aggregates. An in situ hybridization signal is also obtained with the antisense Fuc-TVII probe in a population of cells that line the gut lumenal surface overlying the Peyer's patches. Although these are presumed to be epithelial cells, and may represent so-called M cells (R. L. Owen, *Gastroenterology*, vol. 72, pp. 440-451 (1977)), their precise identity remains unknown.

Figure 5A:
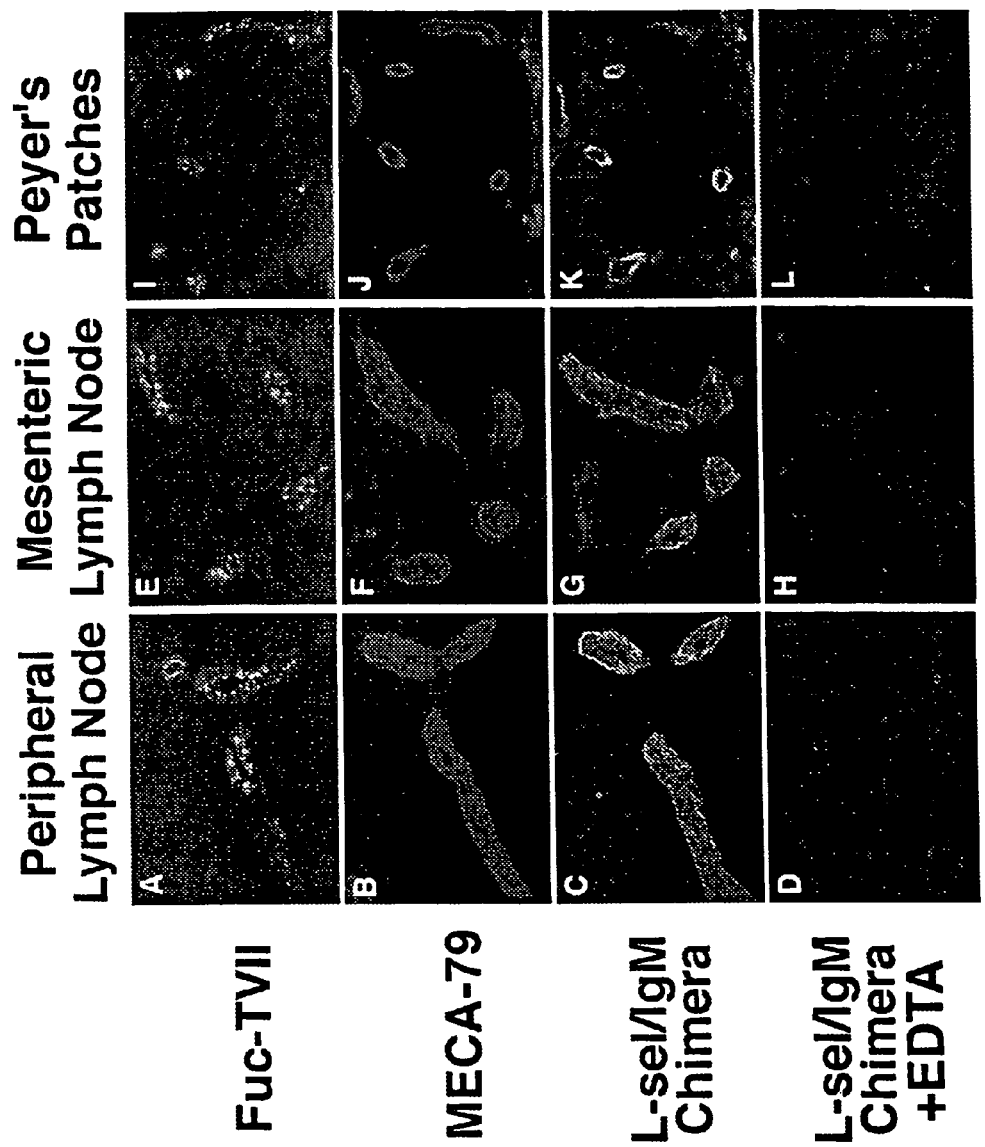
FIGS. 5a and b show the immunohistochemical co-localization of expression of Fuc-TVII, MECA-79, and L-selectin ligands, in lymphoid aggregate high endothelial venular endothelial cells.
Figure 5B:
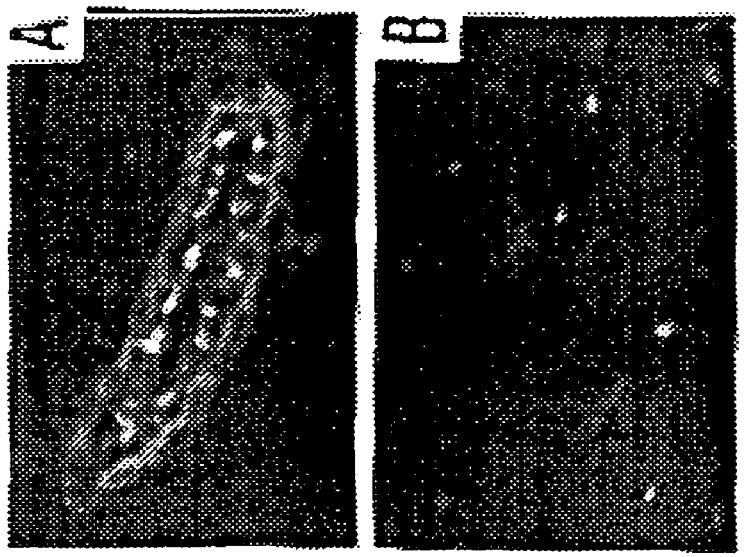
FIG. 5b is a high power magnification of peripheral lymph node HEV staining with anti-Fuc-TVII. Light gray areas in panel A of FIG. 5b correspond to MECA-79 staining. White areas in panel A of FIG. 5b correspond to staining with anti-Fuc-TVII antibody. A 10 micron-thick frozen section of an axillary lymph node was stained simultaneously with the antigen affinity purified anti-Fuc-TVII antibody and with anti-MECA-79 antibody (panel labeled "immune antibodies"). Section-bound antibodies were detected with fluorochrome-conjugated secondary antibody reagents exactly as described in the description of FIG. 5a, and in the Experimental Procedures in the Examples. The immediately adjacent 10 micron-thick frozen section of the same axillary lymph node was instead stained simultaneously with a pair of negative control antibodies (normal rabbit IgG, and normal rat IgM; panel labeled "non-immune antibodies"), and developed in a manner identical to that used in the "immune antibodies" panel. Photomicrographs were taken at 400× magnification, using fluorescent microscopic procedures described in the Experimental Procedures in the Examples.

As noted above, not all Fuc-TVII-derived transcripts yield a protein product. Immunohistochemical analyses were therefore used to confirm that the Fuc-TVII transcripts detected in HEV are accompanied by Fuc-TVII polypeptide expression, and to confirm that such expression co-localizes with L-selectin ligand expression. A rabbit polyclonal antibody raised against the Fuc-TVII peptide yields an intracellular staining pattern in the endothelial cells within HEV in all three lymphoid aggregates (FIG. 5). The perinuclear intracellular staining pattern seen with the anti-Fuc-TVII antibody is consistent with the notion that this enzyme is localized to the Golgi apparatus, where it may participate in the synthesis of fucosylated oligosaccharides with L-selectin ligand activity. In each of the three types of lymphoid aggregate, expression of immunoreactive Fuc-TVII co-localizes with expression of epitopes recognized by the MECA-79 antibody, shown previously to stain HEV, and to interfere with L-selectin binding to HEV (P. R. Streeter et al, *J. Cell Biol.*, vol. 107, pp. 1853-1862 (1988)). Fuc-TVII expression also co-localizes with expression of L-selectin ligands on HEV, as detected with a recombinant mouse L-selectin/human IgM chimeric protein. These observations imply that Fuc-TVII may participate in the synthesis of the sialylated, sulfated, and $\alpha(1,3)$ fucosylated candidate oligosaccharide components of HEV-derived L-selectin ligands.

In an effort to understand the functions of cell surface fucosylated oligosaccharides in animals, we have established a program to isolate murine $\alpha(1,3/4)$fucosyltransferase genes, to be used initially as reagents to characterize tissue-specific expression patterns of the loci that control expression of cell surface fucosylated oligosaccharides. These reagents, and the information gathered from their application will be used eventually with transgenic approaches to uncover functions of their cognate cell surface fucosylated oligosaccharides, by perturbing their expression patterns.

A cross-hybridization approach outlined here yielded a novel genomic sequence that cross-hybridizes with segments derived from the conserved portions of the human Fuc-Ts III, V, and VI genes, in a position corresponding to their catalytic domains. Following the isolation of this murine genomic locus, functional analyses indicated that it encoded an $\alpha(1,3)$ fucosyltransferase, termed Fuc-TVII, with structural features and catalytic activities that were, at the time of its isolation, unique to the $\alpha(1,3)$fucosyltransferase family. In particular, this locus was the only $\alpha(1,3)$fucosyltransferase known to maintain a coding region distributed over more than one exon, and the first fucosyltransferase with multiple distinct initiation codons with the potential to yield structurally distinct polypeptides, characterized by different cytoplasmic domains, but with essentially identical catalytic activities. The catalytic activity of each Fuc-TVII isoenzyme is characterized by an ability to utilize $\alpha 2,3$sialylated type II N-acetyllactosamine precursors, without the ability to utilize neutral type II, neutral type I, or sialylated type I N-acetyllactosamine substrates. Similar observations have been made for the human homologue of Fuc-TVII isolated subsequently (S. Natsuka et al, *J. Biol. Chem.*, vol. 269, pp. 16789-16794 (1994); K. Sasaki et al, *J. Biol. Chem.*, vol. 269, pp. 14730-

14737 (1994)). This catalytic specificity, and the leukocyte-specific expression pattern of this gene, strongly suggest that it plays a pivotal role in the biosynthetic scheme that yields the α2,3-sialylated, α1,3fucosylated lactosaminoglycans essential to E- and P-selectin ligand activity. Furthermore, the leukocytes of mice genetically engineered for a deficiency in this enzyme are deficient in expression of functional ligands for E-selectin and P-selectin, and exhibit a concomitant immune deficiency characterized by a deficit in leukocyte mobilization to inflammatory sites. These observations demonstrate that Fuc-TVII controls leukocyte selectin ligand expression, and indicate that inhibition of this enzyme by pharmaceutical agents or maneuvers will represent an anti-inflammatory approach that may have therapeutic benefit in human disease where selectin-dependent inflammation is pathologic.

Other observations made in the work described here suggest a role for Fuc-TVII in directing synthesis of the oligosaccharide components of the ligands for L-selectin. As Rosen and colleagues have shown, L-selectin ligands on HEV correspond to O-linked carbohydrate determinants displayed by the mucin-type glycoproteins GlyCAM-1, CD34, and MAdCAM-1 (L. A. Lasky et al, *Cell*, vol. 69, pp. 927-938 (1992); S. Baumhueter et al, *Science*, vol. 262, pp. 436-438 (1993); E. L. Berg et al, *Nature*, vol. 366, pp. 695-698 (1993)). Their earlier biochemical analyses indicate that the oligosaccharides relevant to L-selectin ligand activity are sialylated, sulfated, and possibly fucosylated (Y. Imai et al, *J. Cell Biol.*, vol. 113, pp. 1213-1221 (1991)). More recent structural analyses from the Rosen group are consistent with the hypothesis that the capping groups on such oligosaccharides correspond to sulfated versions of the sialyl $sLe^x$ moiety, with sulfate attached via the 6-hydroxyl of the terminal galactose moiety [NeuNAcα2,3($SO_46$)Galβ1,4(Fucα1,3)GlcNAc-R], or via the 6-hydroxyl of the subterminal N-acetyl-glucosamine moiety [NeuNAcα2,3Galβ1,4($SO_46$)(Fucα1,3)GlcNAc-R], or both (S. Hemmerich et al, *Biochemistry*, vol. 33, pp. 4820-4829 (1994); S. Hemmerich et al, *Biochemistry*, vol. 33, pp. 4830-4835 (1994); S. Hemmerich et al, *J. Biol. Chem.*, vol. 270, pp. 12035-12047 (1995)). Non-fucosylated forms of these structures were also identified, however, and the evidence that fucose is required for activity of physiological L-selectin ligands remains circumstantial.

The identification of such non-fucosylated structures suggests the possibility that these sialylated and sulfated molecules represent acceptor substrates for α(1,3)fucosyltransferases expressed in HEV endothelial cells. Our observation that expression of the Fuc-TVII locus co-localizes with L-selectin ligand expression in such cells suggests that Fuc-TVII may operate in this context. Furthermore, mice genetically engineered for a deficiency in Fuc-TVII are deficient in L-selectin-dependent lymphocyte homing to lymph nodes, and are deficient in expression of L-selectin ligand activity on the high endothelial venules in peripheral and mesenteric lymph nodes, and in Peyer's patches. These observations demonstrate that Fuc-TVII controls HEV selectin ligand expression, and indicate that inhibition of this enzyme by pharmaceutical agents or maneuvers will represent an antiinflammatory approach that may have therapeutic benefit in human disease where L-selectin-dependent lymphocyte trafficking is pathologic. The notion that sulfated and sialylated lactosamine moieties represent acceptor substrates for enzymes like Fuc-TVII is supported by studies suggesting that Fuc-TIII (E. V. Chandrasekaran et al, *Biochem. Biophys. Res. Commun.*, vol. 201, pp. 78-89 (1994)) and Fuc-TV (P. R. Scudder et al, *Glycobiology*, vol. 4, pp. 929-933 (1994)) can utilize sialylated, sulfated lactosamine-type acceptors. Indirect evidence derived from studies on the biosynthesis of GlyCAM-1 are also consistent with this hypothesis (S. Hemmerich et al, *Biochemistry*, vol. 33, pp. 4820-4829 (1994); D. Crommie et al, *J. Biol. Chem.*, vol. 270, 22614-22624 (1995)). However, our results indicate that the non-sulfated entity NeuNAcα2,3Galβ1,4GlcNAc is used, in vitro, and in vivo, by Fuc-TVII. Biochemical analyses indicate that 6-0 sulfation of the GlcNAc moiety on this sialylated molecule yields a substance that is used effectively by mouse Fuc-TVII. It therefore remains to be determined if this sulfated molecule or others are utilized by Fuc-TVII, in HEV endothelial cells. Thus, while the biosynthetic scheme for such molecules remains to be defined, it is clear that Fuc-TVII plays an essential role in this pathway.

There is evidence to suggest that L-selectin expressed by granulocytes and other leukocytes mediates adhesion of these cells to activated vascular endothelium through as yet undefined extracellular endothelial cell counterreceptors (M. L. Arbones et al, *Immunity*, vol. 1, pp. 24.7260 (1994); K. Ley et al, *J. Exp. Med.*, vol. 181, pp. 669-675 (1995)). Since the chemical nature of this counter-receptor(s) is not known, a role for Fuc-TVII in the synthesis of such ligands remains speculative, and is a subject of current exploration in this laboratory. In any event, the demonstration here that Fuc-TVII is co-expressed with L-selectin ligands on HEV, when considered together with previous observations demonstrating that Fuc-TVII is expressed in leukocytes and can direct synthesis of ligands for E- and P-selectin, along with evidence that the Fuc-TVII null mice are deficient in ligands for E-, P- and L-selectin, indicates that Fuc-TVII is a master control locus for the synthesis of ligands for all three selecting, and thus for controlling selectin-dependent leukocyte trafficking.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method of preparing a sialyl Lewis x determinant, the method comprising contacting a recombinant murine α(1,3) fucosyltransferase (Fuc-TVII) enzyme catalytic domain with a GDP-fucose donor substrate and a sialyl-N-acetyl-lactosamine acceptor substrate in an enzyme bioreactor under conditions that allow the addition of an α1,3 linked fucose to the sialyl-N-acetyl-lactosamine acceptor substrate, wherein the recombinant murine Fuc-TVII enzyme comprises a catalytic domain is encoded by a nucleic acid sequence segment that is identical to a polynucleotide that is amplified using murine cDNA shown in SEQ ID NO:1 as a template by a 5' primer as shown in SEQ ID NO:3 and a 3' primer as shown in SEQ ID NO:4.

2. The method of claim 1, wherein the Fuc-TVII enzyme catalytic domain is in solution.

3. The method of claim 1, wherein the Fuc-TVII enzyme catalytic domain is immobilized on a solid phase matrix.

4. The method of claim 1, wherein the Fuc-TVII enzyme catalytic domain is produced in a mammalian host cell.

5. The method of claim 1, wherein the Fuc-TVII enzyme catalytic domain is produced in a baculovirus host.

6. The method of claim 1, wherein the sialyl-N-acetyl-lactosamine acceptor is on a glycoprotein.

7. The method of claim 1, wherein the sialyl-N-acetyl-lactosamine acceptor is on a glycolipid.

8. The method of claim 1, wherein the sialyl-N-acetyl-lactosamine acceptor is a free oligosaccharide.

9. A recombinant murine Fuc-TVII enzyme catalytic domain encoded by a nucleic acid sequence segment that is identical to a polynucleotide that is amplified using murine cDNA shown in SEQ ID NO:1 as a template by a 5' primer as shown in SEQ ID NO:3 and a 3' primer as shown in SEQ ID NO:4.

10. A recombinant murine Fuc-TVII enzyme catalytic domain encoded by a nucleic acid segment consisting of residue 2194 to residue 3085 of SEQ ID NO:1.

* * * * *

UNITED STATES PATENT AND TRADEMARK OFFICE
CERTIFICATE OF CORRECTION

PATENT NO. : 7,723,080 B2  Page 1 of 1
APPLICATION NO. : 10/700505
DATED : May 25, 2010
INVENTOR(S) : Shunji Natsuka, Kevin Gersten and John B. Lowe It is certified that error appears in the above-identified patent and that said Letters Patent is hereby corrected as shown below:

Column 37, Line 24 (Claim 1, Line 24), cancel the text "comprises a".

Signed and Sealed this

Seventeenth Day of August, 2010

David J. Kappos
*Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 3594 base pairs (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 1:

```
ACAAACAGGA AGGACAGCAG GCTCTGGCAG CCAGAAGCCT GTGGCCCCAA GCTGGCAGGA      60

TGGCCCCCTT CCTGCAGGTC CCCCACAGCC TTCTGGGTTC CTGACACGAG AGAAGAGGTG     120

GGGCGGGGTG AAGTGAACTC TGAAGCCAAA ATGTGACTCT CCTGGGGTCA CCAGCTTGGG     180

GAGAGGTGAA GAAAGATGCC GGGGCGGAAA CAAAGGGGCA GATATCACTA TGGTTATCTT     240

ACTAAGCACA GAGTAACTGA AAAAGCAAGG GTACCGCTGC CCACCTCGTG CCCACCTTAC     300

GTTATACCTC AAACCAGCTA GATAGTTTCT GATGGCACCC ATACCCTCCC TTCCCCTTTA     360

GGCATTGCGC AAGCTCTCCA CCACAATCTG GAAGTTATAC CCTGCGAGGG GATGGGCAGG     420

GCACTTCTGA GGTGCCAATC AGCCTGCACT CGCCTCTGCC CTGGCCATGG CACTGCTGTC     480

AGTTTCTTGG TACCTGTCTC AACAGCAGCC TTGTCACGTG AGACTATGGC TGGCGGTGGG     540

GGTGGGGGCA GGAATCCTAG AAGCACAGGA GTGACATAGG GTCGGGTCGG GCAGAGCGAA     600

GTGTAGGAGG TGATCCCCAA AGGGATGCTG GGACGATCT GGCCAACACT GTCCTCCCAT      660

TCAAAACTCC CAGTCTGGAG CTCTGGGACA TGGACAAGCC AGGCCTGCTA TTCTCCATAC     720

AGGGCTCCAT AGTGTCTGGC TCAGCAGAGT GGGGGATCTG GTGGGATGG AGGAAGCTTA      780

GCTAAAAGCT TTGTATAGGC TGAAGCTCTG AGTGACCCTG CTGGGCCACC CTACCCTGGT     840

CTGGGCTGGG TCATTGCATC CCCAGATTGG AAGGCTTGGT GAGATGGAGA GGAACCTTGG     900

CTACAAGCTA TAGCTTTGCC CACCAGAGCC TGCTGGAGGG GAATCAAACA AGCCTGGACC     960

TGAGGCTGGG ACTAGCTTTC CTGTTTCTGG AGTGGATGCC AACCCCCTGC CCACCAGCCT    1020

GCCTGTCCAC GCCAGGGACA CACAGACTCC TTCCCTTTCC AGACTGGAAA GCCCCCTCCT    1080

GGGAGAGCAG GAAGGAAGCA ACCTGCAACT CTTCCAGCCC TGGACCTTGG GCTGAACCTA    1140

CAGTTCAAGG TTTGTATGCT CACAGGTCTT GGCAGGGAAA GATAAGAATC CCCAGGGCAC    1200

CCTCCCCCCC GCCCCCCAGT CCACTGCAGG TAGCTCCTGG GTCTGCCCTT CAGGGCAAGT    1260

GCTGACGCTC CATCAGACTG TGATGGGGCC CTTTTCTGAG GATGACAATT CTGAGAACAA    1320

GGCATTTTTC TAGAGGTGGC AGAACAGCAT TTTGTGATGC CGAGGATCT GGGAGCACAG      1380

GTCCAGCTTA ATGAGGGATT GGAGGAAGTG GGTATCATCA TTACAGGGAG GGGCCTCTGT    1440

GGCCTCCTGG GAAAATGCAG TTGCTCTCTT TGGGTGGCCT GGGGTTGTGT GGTGGGCAGA    1500

GGACGGAGGT GCTCATTGGG GGAAGGGATC ACTTCTGCTC AGAGTGCTCG CAAGGGCCTT    1560

TCCTTTTCCT GAAGGCAAGC AGGCCTCCTC CTCCTCCTCT TCCTCCTTCT CCTCTTCCTC    1620

CTCTTTCTCC ATATGCCTAG CTGGTCATTT CTAGGGACCA GCATGGTTGG AAGGGGGCC     1680

TTGTCTTGGC CTTCCTCTTG TCTCAATTCC CTCTTTGAGC AGAAGACGGG GTGGGTGGGG    1740

TAGGATTGGA TAGTGGTTGA TGCCAAAGAT TGAAGGGGTA GGGCGGGGCA GAAGTGGGAA    1800

GGTCCCTGGC TTCCTCACCT TGGTAGATGG TGAGGAGCCC CAGAGGTTGA GCTGAGCAGC    1860

AGCTGTGATT TCAGGGTGCC TCTGTTGGAG AGGCTGCTGT GATTTGAAAA TCTTCTTTCC    1920

TTGGTGACAA TTCAGAAGG CTCCAGATGA ATTGTATTGG TGAGTGCCTG GCCCTTAAGC     1980

AGTCCCAGCT GGGGATGATG GGGATTTATG GGTGTCCCTG AGCCTAGGGT GACAGGGCCT    2040

CTCCTTTTTT TTTTATTCTG CTTCAGGGTA CCACCCCACC AGGAGGCTGC GGGCCTGGGG    2100

CGGCCTAGCT GGAGGAGCAA CATTCATGGT AATTTGGTTT TTCTGGCTGT GGGGATCAGC    2160
```

```
TCCTGGAAGT GCCCCTGTGC CTCAGTCCAC ACTCACCATC CTTATCTGGC ACTGGCCTTT    2220

CACCAACCGG CCGCCAGAGC TACCTGGTGA CACCTGCACT CGCTATGGCA TGGCCAGCTG    2280

CCGTCTGAGT GCTAACCGGA GCCTGCTAGC CAGTGCTGAT GCTGTGGTCT TCCACCACCG    2340

TGAGCTGCAA ACCCGGCAAT CTCTCCTACC CCTGGACCAG AGGCCACACG GACAGCCTTG    2400

GGTCTGGGCC TCCATGGAAT CGCCCAGTAA TACCCATGGT CTCCATCGCT TCCGGGGCAT    2460

CTTCAACTGG GTGCTGAGCT ATCGGCGTGA TTCAGATATC TTTGTACCCT ACGGTCGCTT    2520

GGAGCCTCTC TCTGGGCCCA CATCCCCACT ACCGGCCAAA AGCAGGATGG CTGCCTGGGT    2580

GATCAGCAAT TCCAGGAGC GGCAGCAGCG TGCAAAGCTG TACCGGCAGC TGGCCCCTCA     2640

TCTGCAGGTG GATGTGTTCG GTCGCGCCAG CGGACGGCCC CTATGCGCTA ATTGTCTGCT    2700

GCCCACTTTG GCCCGGTACC GCTTCTACCT GGCCTTTGAG AACTCACAGC ATCGGGACTA    2760

CATCACTGAG AAGTTCTGGC GCAATGCCCT GGCGGCTGGT GCTGTACCCG TGGCGCTGGG    2820

ACCTCCTCGG GCCACCTACG AGGCTTTTGT GCCACCAGAT GCCTTTGTAC ACGTGGACGA    2880

CTTCAGCTCT GCCCGTGAAC TGGCTGTCTT CCTCGTCAGC ATGAATGAGA GTCGTTATCG    2940

TGGCTTCTTT GCTTGGCGAG ACCGGCTCCG TGTGCGGCTC CTGGGTGACT GGAGGGAGCG    3000

CTTCTGCACC ATCTGTGCCC GCTACCCTTA CTTGCCCCGC AGCCAGGTCT ATGAAGACCT    3060

TGAAAGCTGG TTCCAGGCTT GAACTCCTGC TGCTGGGAGA GGCTGGATGG GTGGGAGACT    3120

GATGTTGAAA CCAAAGAGCT GGGCATCCAG GCTTTTGGTC ACCATGGCAC TACCCCAAGG    3180

CTTTTCCTGT TCAGTGAGCA GGAATTCAGG ATATAAGGAG AAGACTGGGC TGAGATACCC    3240

TGGTGGGCTT TAGAGTAGGG GCCCAGGATA AGAGACAATG AATTAATGAG GAGCATATGG    3300

GGAAGGTGGC TGAGGGTCCC TGACTTACCT TGACCCATGG CTGAAGGCTC CATGCCCATG    3360

GCTGGAGCTG GGACCCTACA CTTCTATAGT CAAGGTGCTT AGCCTCAAGG TTGCAGATGC    3420

ACCCTCTAGT ACTCTGGGTG CAGACTGTAC ACTGGGCGCA GGGGGTTGTG GAAGGACAGT    3480

GCAGATGATT CTGGGCTTTT GACACCACAG TTCCCCCAGG GAAAGAGGCA CTACTAATAA    3540

AAACACTGAC AGAAATCTCC TGGTCAAGTC TGTTAGGCAG CAGAGCTCGA ATTC          3594

(2) INFORMATION FOR SEQ ID NO: 2:

(i) SEQUENCE CHARACTERISTICS:
        (A) LENGTH: 393 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2:

Met Pro Thr Pro Cys Pro Pro Ala Cys Leu Ser Thr Pro Gly Thr His
1               5                   10                  15

Arg Leu Leu Pro Phe Pro Asp Trp Lys Ala Pro Ser Trp Glu Ser Arg
                20                  25                  30

Lys Glu Ala Thr Cys Asn Ser Ser Pro Gly Pro Trp Ala Glu Pro
        35                  40                  45

Thr Val Gln Met Asn Cys Ile Gly Tyr His Pro Thr Arg Arg Leu Arg
        50                  55                  60

Ala Trp Gly Gly Leu Ala Gly Gly Ala Thr Phe Met Val Ile Trp Phe
65                  70                  75                  80

Phe Trp Leu Trp Gly Ser Ala Pro Gly Ser Ala Pro Val Pro Gln Ser
                85                  90                  95
```

```
Thr Leu Thr Ile Leu Ile Trp His Trp Pro Phe Thr Asn Arg Pro Pro
            100                 105                 110

Glu Leu Pro Gly Asp Thr Cys Thr Arg Tyr Gly Met Ala Ser Cys Arg
            115                 120                 125

Leu Ser Ala Asn Arg Ser Leu Leu Ala Ser Ala Asp Ala Val Val Phe
            130                 135                 140

His His Arg Glu Leu Gln Thr Arg Gln Ser Leu Leu Pro Leu Asp Gln
145                 150                 155                 160

Arg Pro His Gly Gln Pro Trp Val Trp Ala Ser Met Glu Ser Pro Ser
                165                 170                 175

Asn Thr His Gly Leu His Arg Phe Arg Gly Ile Phe Asn Trp Val Leu
            180                 185                 190

Ser Tyr Arg Arg Asp Ser Asp Ile Phe Val Pro Tyr Gly Arg Leu Glu
            195                 200                 205

Pro Leu Ser Gly Pro Thr Ser Pro Leu Pro Ala Lys Ser Arg Met Ala
    210                 215                 220

Ala Trp Val Ile Ser Asn Phe Gln Glu Arg Gln Gln Arg Ala Lys Leu
225                 230                 235                 240

Tyr Arg Gln Leu Ala Pro His Leu Gln Val Asp Val Phe Gly Arg Ala
                245                 250                 255

Ser Gly Arg Pro Leu Cys Ala Asn Cys Leu Leu Pro Thr Leu Ala Arg
            260                 265                 270

Tyr Arg Phe Tyr Leu Ala Phe Glu Asn Ser Gln His Arg Asp Tyr Ile
            275                 280                 285

Thr Glu Lys Phe Trp Arg Asn Ala Leu Ala Ala Gly Ala Val Pro Val
    290                 295                 300

Ala Leu Gly Pro Pro Arg Ala Thr Tyr Glu Ala Phe Val Pro Pro Asp
305                 310                 315                 320

Ala Phe Val His Val Asp Asp Phe Ser Ser Ala Arg Glu Leu Ala Val
                325                 330                 335

Phe Leu Val Ser Met Asn Glu Ser Arg Tyr Arg Gly Phe Phe Ala Trp
            340                 345                 350

Arg Asp Arg Leu Arg Val Arg Leu Leu Gly Asp Trp Arg Glu Arg Phe
            355                 360                 365

Cys Thr Ile Cys Ala Arg Tyr Pro Tyr Leu Pro Arg Ser Gln Val Tyr
    370                 375                 380

Glu Asp Leu Glu Ser Trp Phe Gln Ala
385                 390

(2) INFORMATION FOR SEQ ID NO: 3:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC PRIMER"

(xi) SEQUENCE DESCRIPTION: SEQ ID NO: 3:

GCGCGGATCC CACCATCCTT ATCTGGCACT GGCCTTTCAC C                  41

(2) INFORMATION FOR SEQ ID NO: 4:

(i) SEQUENCE CHARACTERISTICS:
        (A) LENGTH: 44 base pairs
```

```
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SYNTHETIC PRIMER"

(xi) SEQUENCE DESCRIPTION: SEQ ID NO: 4:

GCGCGGATCC AGTTCAAGCC TGGAACCAGC TTTCAAGGTC CTTC                    44
```